(12) United States Patent
Kovacs et al.

(10) Patent No.: US 11,130,729 B2
(45) Date of Patent: Sep. 28, 2021

(54) CCL2 INHIBITORS

(71) Applicant: LAPKO INC., Las Vegas, NV (US)

(72) Inventors: Bruce Kovacs, Long Beach, CA (US); Kamron Shahbahrami, Irvine, CA (US); George Nicola, La Jolla, CA (US)

(73) Assignee: LAPKO INC., Las Vegas, NV (US)

( * ) Notice: Subject to any disclaimer, the term of this patent is extended or adjusted under 35 U.S.C. 154(b) by 0 days.

(21) Appl. No.: 16/620,493

(22) PCT Filed: Jun. 12, 2018

(86) PCT No.: PCT/US2018/037061
§ 371 (c)(1),
(2) Date: Dec. 7, 2019

(87) PCT Pub. No.: WO2018/231795
PCT Pub. Date: Dec. 20, 2018

(65) Prior Publication Data
US 2020/0181062 A1 Jun. 11, 2020

Related U.S. Application Data

(60) Provisional application No. 62/518,929, filed on Jun. 13, 2017.

(51) Int. Cl.
*C07C 217/22* (2006.01)
*C07D 295/13* (2006.01)
*A61K 45/06* (2006.01)

(52) U.S. Cl.
CPC .......... *C07C 217/22* (2013.01); *C07D 295/13* (2013.01); *A61K 45/06* (2013.01)

(58) Field of Classification Search
CPC .......................... C07C 217/22; C07D 295/13
See application file for complete search history.

(56) References Cited

U.S. PATENT DOCUMENTS

2010/0226943 A1* 9/2010 Brennan .............. A41D 31/305
424/400

FOREIGN PATENT DOCUMENTS

| GB | 1100936 A | 1/1968 |
| GB | 1287433 A | 8/1972 |
| GB | 2064522 B | 5/1983 |
| WO | 2018067638 A3 | 5/2019 |

OTHER PUBLICATIONS

Thuillier, et al. Document No. 59:35302 retrieved from STN, 1963.*
Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Cambien B, et al., "Signal transduction involved in MCP-1-mediated monocytic transendothelial migration", Blood Jan. 15, 2001;97(2):359-66.
Ahad MA, et al., "Polymorphisms of chemokine and chemokine receptor genes in idiopathic immune-mediated posterior segment uveitis" Mol Vis. Mar. 23, 2007;13:388-96.
Ashida N, et al., "Distinct Signaling Pathways for MCP-1dependent Intergin Activation and Chemotaxis", Jornal of Biological Chemistry, 2001, vol. 276, No. 19, pp. 16555-16560.
Bauvois B., "Transmembrane proteases in cell growth and invasion: new contributors to angiogenesis?", Oncogene Jan. 15, 2004;23(2):317-29.
Bidzhekov K, et al., "MCP-1 Induces a Novel Transcription Factor With Proapoptotic Activity", Circulation Res May 12, 2006;98(9):1107-9.
Biswas SK & Sodhi A, "Tyrosine phosphorylation-mediated signal transduction in MCP-1-induced macrophage activation: role for receptor dimerization, focal adhesion protein complex and JAK/STAT pathway", International Immunopharm Jul. 2002;2(8):1095-107.
Biswas SK & Sodhi A., "In Vitro Activation of Murine Peritoneal Macrophages by Monocyte Chemoattractant Protein-1: Upregulation of CD11b, Production of Proinflammatory Cytokines, and the Signal Transduction Pathway", Interferon & cytokine research May 2002;22(5):527-38.
Biswas SK, et al., "Regulation of Nitric Oxide Production by Murine Peritoneal Macrophages Treated in Vitro with Chemokine Monocyte Chemoattractant Protein 1", Nitric Oxide Dec. 2001;5(6):566-79.
Cain R and Ridley A., "Phosphoinositide 3-kinases in cell migration", Biology of the Cell, 2009, 101(1):13-29.
Carr MW, et al., "The C-C Chemokine MCP-1 Differentially Modulates the Avidity of b1 and b2 Integrins on T Lymphocytes", Immunity Feb. 1996;4(2):179-87.
Charo IF, et al., "The Many Roles of Chemokines and Chemokine Receptors in Inflammation", N Eng. J Med, 2006, 354:610-21.
Cho ML, et al., "The MCP-1 Promoter 22518 Polymorphism in Behcet's Disease: Correlation Between Allele Types, MCP-1 Production and Clinical Symptoms among Korean Patients", Autoimmunity. Feb. 2004;37(1):77-80.
Comerford I, et al., "Regulation of chemotactic networks by 'atypical' receptors", BioEssays Mar. 2007;29 (3):237-47.
Curnock AP, et al., "Chemokine signaling: pivoting around multiple phosphoinositide 3-kinases", Immunology, 2002, 105(2):125-36.
Dawson J, et al., "Targeting monocyte chemoattractant protein-1 signalling in disease", Expert opinion on therapeutic targets Feb. 2003;7(1):35-48.
Denis C, et al., "Probing Heterotrimeric G Protein Activation: Applications to Biased Ligands" Current Pharm Design 2012;18(2):128-44.
Deshmane SL, et al., "Monocyte Chemoattractant Protein-1 (MCP-1): An Overview" J Interferon & Cytokine Research Jun. 2009;29(6):313-26.
Dimberg A., "Chemokines in Angiogenesis", Current topics in microbiology and immunology 2010;341:59-80.

(Continued)

*Primary Examiner* — Shawquia Jackson
(74) *Attorney, Agent, or Firm* — Gorman IP Law, APC

(57) ABSTRACT

Compounds, pharmaceutically acceptable salts, and pharmaceutical compositions thereof are disclosed that are useful for inhibition of the biological activity of CCL2, as well as methods of treatment for diseases involving the biological activity of CCL2.

15 Claims, 7 Drawing Sheets

(56) References Cited

OTHER PUBLICATIONS

Figure 1A:
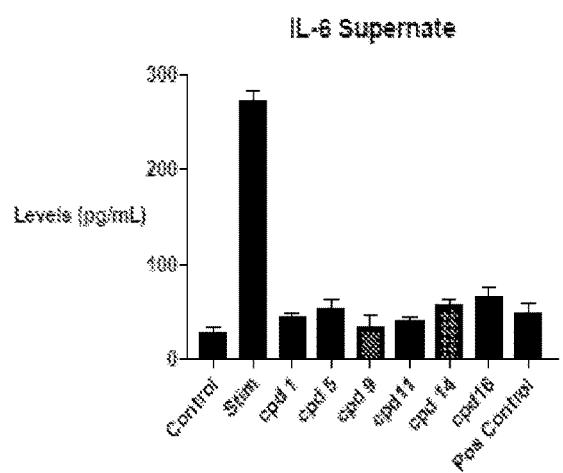
Figure 1B:
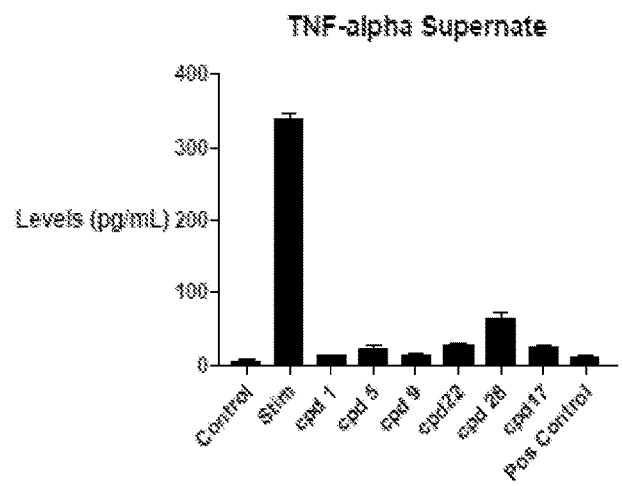
Figure 1C:
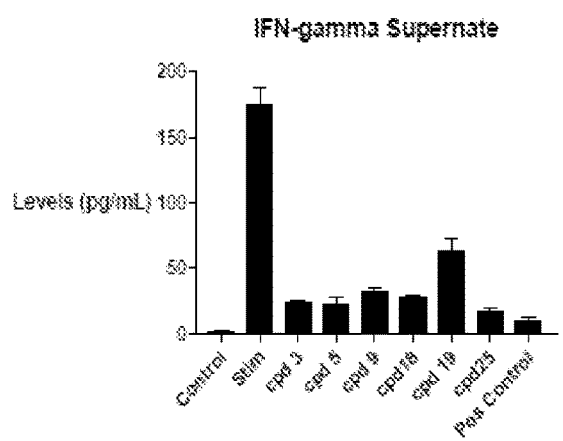
Figure 1D:
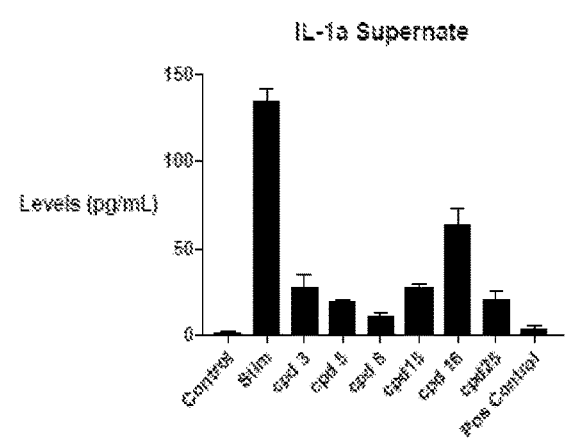

Fenoglio C, et al., "MCP-1 in Alzheimer's disease patients: A-2518G polymorphism and serum levels", Neurobiol Aging. Oct. 2004;25(9):1169-73.

Ferreira AM, et al., "The p110σ Isoform of PI3K Differentially Regulates β1 and β2 Integrin-Mediated Monocyte Adhesion and Spreading and Modulates Diapedesis", Microcirculation Sep. 2006;13(6):439-56.

Fra AM, at al., "Cutting Edge: Scavenging of Inflammatory CC Chemokines by the Promiscuous Putatively Silent Chemokine Receptor D61" J Immunol Mar. 1, 2003;170(5):2279-82.

Fujimoto H, et al., "Stromal MCP-1 in mammary tumors induces tumor-associated macrophage infiltration and contributes to tumor progression", Int J Cancer Sep. 15, 2009;125(6):1276-84.

Galvez BG, et al., "Membrane Type 1-Matrix Metalloproteinase Is Regulated by Chemokines Monocyte-Chemoattractant Protein-1/CCL2 and Interleukin-8/CXCL8 in Endothelial Cells during Angiogenesis" J Biol Chem Jan. 14, 2005;280(2):1292-8.

Gavrilin MA, et al., "Monocyte Chemotactic Protein 1 Upregulates Il-1b Expression in Human Monocytes", Biochem Biophys Res Com Oct. 14, 2000;277(1):37-42.

Gerszten RE, et al., "role of Phosphoinositide 3-kinase in Monocyte Recruitment under Flow Conditions", J Biol Chem, Jul. 20, 2001;276(29):26846-51.

Gielsdorf W., "Beitrag zu biotransformation und analytik des psychopharmacons mefexamid", Zeitschrift fur Rechtsmedizin, 1981, vol. 87, pp. 117-127.

Giunti S, et al., "The MCP-1/CCR2 system has direct proinflammatory effects in human mesangial cells", Kidney Internat Mar. 2006;69(5):856-63.

Hartl D, et al., "A role for MCP-1/CCR2 in interstitial lung disease in children Dominik Hartl1, Matthias Griese1, Thomas Nicolai1, Gernot Zissel2, Christine Prell1, Dietrich Reinhardtl, Dolores J Schendel3 and Susanne Krauss-Etschmann", Respir Res. Aug. 11, 2005;6:93.

Hawkins PT, et al., "Signalling through Class I PI3Ks in mammalian cells", Biochem Society Trans, 2006, 34(Pt 5):647-62.

Hong KH, et al., "Monocyte chemoattractant protein-1-induced angiogenesis is mediated by vascular endothelial growth factor-A", Blood, 2005, 15;105(4):1405-7.

International Search Report dated Oct. 2, 2018.

Iwamoto N, et al., "Regulation of disease susceptibility and mononuclear cell infiltration into the labial salivary glands of S gren's syndrome by monocyte chemotactic protein-1" Rheumatology (Oxford). Aug. 2010;49(8):1472-8.

Jiang Y, et al., "Monocyte chemoattractant protein-1 regulates adhesion molecule expression and cytokine production in human monocytes", J Immunology Apr. 15, 1992;148(8):2423-8.

Jimenez-Sainz MC, et al., "Signaling Pathways for Monocyte Chemoattractant Protein 1-Mediated Extracellular Signal-Regulated Kinase Activation", Mol Pharmacology, 2003, 64(3):773-82.

Karrer S, et al., "The -2518 Promotor Polymorphism in the MCP-1 Gene Is Associated with Systemic Sclerosis", J Invest Dermatol. Jan. 2005;124(1):92-8.

Kashiwazaki M, et al., "A high endothelial venule-expressing promiscuous chemokine receptor DARC can bind inamatory, but not lymphoid, chemokines and is dispensable for lymphocyte homing under physiological conditions", International immunology, 2003,(10):1219-27.

Ke Q & Costa M, "Hypoxia-Inducible Factor-1 (HIF-1)", Mol Pharmacology Nov. 2006;70(5):1469-80.

Kleinert H, et al. "Regulation of the expression of inducible nitric oxide synthase", Euro J Pharmacol Oct. 1, 2004;500 (1-3):255-66.

Kolluri R, et al., "Direct interaction of the Wiskott-Aldrich syndrome protein with the GTPase Cdc42", PNAS (USA) May 28, 1996;93(11):5615-8.

Lai CH, et al., "Critical role of actin in modulating BBB permeability" Brain research reviews Dec. 1, 2005;50(1):7-13.

Letendre S, et al., "The monocyte chemotactic protein-1-2578G allele is associated with elevated MCP-1 concentrations in cerebrospinal fluid" J Neuroimmunol. Dec. 2004;157(1-2):193-6.

Liu H, et al., "TNF-a Gene Expression in Macrophages: Regulation by NF-kB Is Independent of c-Jun or C/EBPb1", J Immunology Apr. 15, 2000;164(8):4277-85.

Maus U, et al., "Role of endothelial MCP-1 in monocyte adhesion to inflamed human endothelium under physiological flow", American J Physiol., 2002, 283(6):H2584-91.

Mehrad B, et al., "Chemokines as mediators of angiogenesis", Thrombo Haemost May 2007;97(5):755-62.

Mehta NN, et al., "Modulation of cardiometabolic pathways in skin and serum from patients with psoriasis", J Transl Med. Aug. 22, 2013;11:194.

Miotto D, et al., "Expression of IFN-γ-inducible protein; monocyte chemotactic proteins 1, 3, and 4; and eotaxin in TH1- and TH2-mediated lung diseases", J Allergy Clin Immunol. Apr. 2001;107(4):664-70.

Monteclaro FS, et al., "The Amino-terminal Domain of CCR2 Is Both Necessary and Sufficient for High Affinity Binding of Monocyte Chemoattractant Protein 1", J Biol Chem 1997, 272(37):23186-90.

Mori H, et al., "Monocyte chemoattractant protein-1 A-2518G gene polymorphism and renal survival of Japanese patients with immunoglobulin A nephropathy", Clin Exp Nephrol. Dec. 2005;9(4):297-303.

Mukai Y, et al., "Involvement of Arp2/3 complex in MCP-1-induced chemotaxis", Biochem Biophys Res Comm Aug. 26, 2005;334(2):395-402.

Nagalakshmi U, et al., "RNA-Seq: A Method for Comprehensive Transcriptome Analysis", Curr Protoc Mol Biol. Jan. 2010; 4.11.1-4.11.13.

Norris M., et al., "Monocyte chemoattractant protein-1 is excreted in excessive amounts in the urine of patients with lupus nephritis", Lab Invest, Dec. 1995; 73(6):804-9—Abstract.

Nibbs R, et al., "Cloning and Characterization of a Novel Murine b Chemokine Receptor, D6", J Biol Chem, 1997, 9;272(19):12495-504.

Niu J, et al., "Monocyte Chemotactic Protein (MCP)-1 Promotes Angiogenesis via a Novel Transcription Factor, MCP-1-induced Protein (MCPIP)", J Biol Chem May 23, 2008;283(21):14542-51.

Oda N, et al., "ETS-1 Converts Endothelial Cells to the Angiogenic Phenotype by Inducing the Expression of Matrix Metalloproteinases and Integrin b3" J Cell Physiology Feb. 1999;178(2):121-32.

Pahl HL, "Activators and target genes of Rel/NF-kB transcription factors", Oncogene Nov. 22, 1999;18(49):6853-66.

Papachristou GI, et al., "Is the Monocyte Chemotactic Protein-1 2518 G Allele a Risk Factor for Severe Acute Pancreatitis?", Clin Gastroenterol Hepatol. May 2005;3(5):475-81.

Park BL, et al., "Association of common promoter polymorphisms of MCP1 with hepatitis B virus clearance", Exp Mol Med. Dec. 31, 2006;38(6):694-702.

Pepper MS, "Role of the Matrix Metalloproteinase and Plasminogen Activator-Plasmin Systems in Angiogenesis", Arteriosclerosis, thrombosis, and vascular biology Jul. 2001;21(7):1104-17.

Pulverer BJ, et al., "Phosphorylation of c-jun mediated by MAP kinases", Nature Oct. 17, 1991;353(6345):670-4.

Richard DE, et al., "p42/p44 Mitogen-activated Protein Kinases Phosphorylate Hypoxia-inducible Factor 1a (HIF-1a) and Enhance the Transcriptional Activity of HIF-1", J Biol Chem Nov. 12, 1999;274(46):32631-7.

Rollins BJ, et al., "Recombinant Human MCP-1/JE Induces Chemotaxis, Calcium Flux, and the Respiratory Burst in Human Monocytes ", Blood Aug. 15, 1991;78(4):1112-6.

Roy A, Kolattukudy PE., "Monocyte chemotactic protein-induced protein (MCPIP) promotes inflammatory angiogenesis via sequential induction of oxidative stress, endoplasmic reticulum stress and autophagy", Cellular Signalling Nov. 2012;24(11):2123-31.

(56) References Cited

OTHER PUBLICATIONS

Rozyk KJ, et al., "Monocyte chemotactic and activating factor/monocyte chemoattractant protein in bronchoalveolar lavage fluid from patients with atopicasthma and chronic bronchitis Relationship to lung function tests, bronchial hyper-responsiveness and cytology of bronchoalveolar lavage fluid", Immunol Lett. Jun. 1997;58(1):47-52.

Schneeberger EE & Lynch RD., "The tight junction: a multifunctional complex" Am J Physiology Jun. 2004;286 (6):C1213-28.

Sierra-Filardi, et al., "CCL2 Shapes Macrophage Polarization by GM-CSF and M-CSF: Identification of CCL2/CCR2-Dependent Gene Expression Profile", J Immunol. Apr. 15, 2014, 192 (8) 3858-3867.

Song L & Pachter JS., "Monocyte chemoattractant protein-1 alters expression of tight junction-associated proteins in brain microvascular endothelial cells", Microvascular Res Jan. 2004;67(1):78-89.

Song L, et al., "Caveolin-1 regulates expression of junction-associated proteins in brain microvascular endothelial cells", Blood Feb. 15, 2007;109(4):1515-23.

Sorensen TL, et al. "Chemokine CCL2 and chemokine receptor CCR2 in early active multiple sclerosis", Eur J Neurol. Jul. 2004;11(7):445-9.

Sotsios Y & Ward SG, "Phosphoinositide 3-kinase: a key biochemical signal for cell migration in response to chemokines" Immunological reviews Oct. 2000;177:217-35.

Sozzani S, et al., "Receptors, signal transduction, and spectrum of action of monocyte chemotactic protein-1 and related chemokines", J Leukocyte Biol, 1995;57(5):788-94.

Stamatovic SM, et al., "Caveolae-mediated Internalization of Occludin and Claudin-5 during CCL2-induced Tight Junction Remodeling in Brain Endothelial Cells", J Biol Chem Jul. 10, 2009;284(28):19053-66.

Stamatovic SM, et al., "CCL2 Regulates Angiogenesis via Activation of Ets-1 Transcription Factor1", J Immunology Aug. 15, 2006;177(4):2651-61.

Stamatovic SM, et al., "Monocyte chemoattractant protein-1 regulation of blood-brain barrier permeability", J Cerebral blood flow and metabolism May 2005;25(5):593-606.

Stamatovic SM, et al., "Potential role of MCP-1 in endothelial cell tight junction 'opening': signaling via Rho and Rho kinase ", J Cell Sci Nov. 15, 2003;116(Pt 22):4615-28.

Stamatovic SM, et al., "Protein Kinase C-RhoA Cross-talk in CCL2-induced Alterations in Brain Endothelial Permeability", J Biol Chem Mar. 31, 2006;281(13):8379-88.

Tabara Y, et al., "Polymorphism of the Monocyte Chemoattractant Protein (MCP-1) Gene Is Associated with the Plasma Level of MCP-1 But Not with Carotid Intima-Media Thickness", Hypertens Res. Sep. 2003;26(9):677-83.

Tesch GH., "MCP-1/CCL2: a new diagnostic marker and therapeutic target for progressive renal injury in diabetic nephropathy", Am J Physiology. Renal physiology Apr. 2008;294(4):F697-701.

Trapnell C, et al., "Differential analysis of gene regulation at transcript resolution with RNA-seq", Nat Biotechnol. Jan. 2013; 34(1): 46-53.

Turner S, et al., "The CC Chemokine Monocyte Chemotactic Peptide-1 Activates both the Class I p85/p110 Phosphatidylinositol 3-Kinase and the Class II PI3K-C2α", J Biol Chem, 1998, 273(40):25987-95.

Vestergaard C, et al., "Expression of CCR2 on Monocytes and Macrophages in Chronically Inflamed Skin in Atopic Dermatitis and Psoriasis", Acta Derm Venereol. 2004; 84: 353-358.

Viedt C & Orth SR., "Monocyte chemoattractant protein-1 (MCP-1) in the kidney: does it more than simply attract monocytes?", Nephrology, dialysis, transplantation Dec. 2002;17(12):2043-7.

Viedt C, et al., MCP-1 Induces Inflammatory Activation of Human Tubular Epithelial Cells: Involvement of the Trascription Factors, Nuclear Factor kB and Activating Protein-1, JASN, 2002;13(6):1534-47.

Viedt C, et al., "Monocyte Chemoattractant Protein-1 Induces Proliferation and Interleukin-6 Production in Human Smooth Muscle Cells by Differential Activation of Nuclear Factor-B and Activator Protein-1", Arterio Thromb Vasc Biol Jun. 1, 2002;22(6):914-20.

Wain JH, et al., "Leucocyte chemotaxis: Examination of mitogen-activated protein kinase and phosphoinositide 3-kinase activation by Monocyte Chemoattractant Proteins-1, -2, -3 and -4", Clin Exp Immunology Mar. 2002;127(3):436-44.

Wang C, et al., "A comprehensive study design reveals treatment- and transcript abundance-dependent concordance between RNA-seq and microarray data", Nat Biotechnol. Aug. 2014; 32: 926-932.

Weber C, et al., "Sequential Regulation of $\alpha 4\beta 1$ and $\alpha 5\beta 1$ Integrin Avidity by CC Chemokines in Monocytes: Implication for Transcndothelial Chemotaxis", J Cell Biol, Aug. 1996;134(4):1063-73.

Weber KS, et al., "Chemokine-induced monocyte transmigration requires cdc42-mediated cytoskeletal changes", Euro J Immunol Jul. 1998;28(7):2245-51.

Weber KS, et al., "Specific Activation of Leukocyte b2 Integrins Lymphocyte Function—associated Antigen-1 and Mac-1 by Chemokines Mediated by Distinct Pathways via the a Subunit Cytoplasmic Domains", Mol Biol Cell Apr. 1999;10(4):861-73.

Welch HC, et al., "Phosphoinositide 3-kinase-dependent activation of Rac", FEBS letters Jul. 3, 2003;546(1):93-.

Werle M, et al., "M CP-1 induces activation of MAP-kinases ERK, JNK and p38 MAPK in human endothelial cells", J. Cardiovascular Res Nov. 2002;56(2):284-92.

Written Opinion dated Oct. 2, 2018.

Wymann MP & Pirola L, "Structure and function of phosphoinositide 3-kinases", Biochimica et biophysica acta Dec. 8, 1998;1436(1-2):127-50.

Yadav A, et al., "MCP-1: Chemoattractant with a role beyond immunity: A review", Clinica chimica acta; Nov. 11, 2010;411(21-22)1570-9.

Yamamoto T, et al., "Monocyte Chemoattractant Protein-1 Enhances Gene Expression and Synthesis of Matrix Metalloproteinase-1 in Human Fibroblasts by an Autocrine IL-1a Loop1", J Immunology Jun. 15, 2000;164(12):6174-9.

Yang EJ, et al., "Differential Effect of CCL2 on Constitutive Neutrophil Apoptosis Between Normal and Asthmatic Subjects", J Cell Physiology Jun. 2012;227(6):2567-77.

Yoon S & Seger R, "The extracellular signal-regulated kinase: Multiple substrates regulate diverse cellular functions", Growth Factors Mar. 2006;24(1):21-44.

Younce CW & Kolattukudy PE, "MCP-1 causes cardiomyoblast death via autophagy resulting from ER stress caused by oxidative stress generated by inducing a novel zinc-fingerprotein, MCPIP", Biochem Journal Jan. 27, 2010,426(1):43-53.

Younce CW, et al., "Hyperglycaemia-induced cardiomyocyte death is mediated via MCP-1 production and induction of a novel zinc-finger protein MCPIP", Cardiovascular Res Sep. 1, 2010;87(4):665-74.

Zhang L, et al., "Chemokine Signaling Pathway Involved in CCL2 Expression in Patients with Rheumatoid Arthritis", Yonsei Med J. Jul. 2015;56(4):1134-42.

Zhang X et al., "Monocyte chemoattractant protein-1 induces endothelial cell apoptosis in vitro through a p53-dependent mitochondrial pathway", Acta biochimica et biophysica Sinica Oct. 2011;43(10):787-95.

Zhou L, et al., "Monocyte Chemoattractant Protein-1 Induces a Novel Transcription Factor That Causes Cardiac Myocyte Apoptosis and Ventricular Dysfunction", Circulation Res May 12, 2006;98(9):1177-85.

* cited by examiner

Table 1 Example compounds R Table

| | Cpd1 | Cpd 2 | Cpd3 | Cpd 4 | Cpd 5 | Cpd 6 |
|---|---|---|---|---|---|---|
| R1 | H | H | H | $CH_3$ | H | H |
| R2 | $CH3$ | $CH_2CH_3$ | $CH_2CH_3$ | $CH3$ | $CH_2CH_3$ | $CH_2CH_2F$ |
| R2' | $CH3$ | $CH_3$ | $CH_2CH_2F$ | $C_3H_7$ | $CH_2CH_3$ | $CH_3$ |
| R3 | COOH | COOH | $OCH_3$ | $OCH_2CH_3$ | OH | $OCH_3$ |
| R4 | H | F | H | OH | H | H |
| X = | 2 | 2 | 2 | 2 | 2 | 2 |
| Y = | 2 | 2 | 2 | 2 | 2 | 2 |

| | Cpd 7 | Cpd 8 | Cpd 9 | Cpd 10 | Cpd 11 | Cpd 12 |
|---|---|---|---|---|---|---|
| R1 | H | H | $CH_3$ | $CH_3$ | H | $CH_2CH_3$ |
| R2 | $CH_2CH_3$ | $CH3$ | $C_4H_8N$ | $CH_2CH_3$ | $C_4H_4N$ | $CH_2CH_3$ |
| R2' | $CH_2CH_3$ | $CH_2CH_3$ | n/a | $CH_2CH_2OH$ | n/a | $CH_2CH_3$ |
| R3 | $OCH_3$ | $OCH_2CH_3$ | $OCH_3$ | $OCH_3$ | OH | $OCH_3$ |
| R4 | H | OH | H | H | F | H |
| X = | 2 | 2 | 2 | 2 | 2 | 2 |
| Y = | 2 | 2 | 2 | 2 | 2 | 2 |

| | Cpd 13 | Cpd 14 | Cpd 15 | Cpd 16 | Cpd 17 |
|---|---|---|---|---|---|
| R1 | H | $CH3$ | H | H | H |
| R2 | $C_4H_4N$ | $C_5H_{10}N$ | $C_5H_{10}N$ | $C_4H_8NO$ | $CH_2CH_3$ |
| R2' | n/a | n/a | n/a | n/a | $CH_2CH_3$ |
| R3 | $CH_2COOH$ | $OCH_3$ | $OCH_3$ | $OCH_3$ | $OCH_3$ |
| R4 | H | H | H | H | F |
| X = | 2 | 2 | 2 | 2 | 2 |
| Y = | 2 | 2 | 2 | 2 | 2 |

| | Cpd 21 | Cpd 22 | Cpd 23 | Cpd 24 | Cpd 25 | Cpd 26 |
|---|---|---|---|---|---|---|
| R1 | H | H | H | $CH_3$ | H | H |
| R2 | $CH3$ | $CH_2CH_3$ | $CH_2CH_3$ | $CH3$ | $CH_2CH_3$ | $CH_2CH_2F$ |
| R2' | $CH3$ | $CH_3$ | $CH_2CH_2F$ | $C_3H_7$ | $CH_2CH_3$ | $CH_3$ |
| R3 | COOH | COOH | $OCH_3$ | $OCH_2CH_3$ | OH | $OCH_3$ |
| R4 | H | F | H | OH | H | H |
| X = | 1 | 1 | 2 | 1 | 2 | 2 |
| Y = | 2 | 2 | 3 | 2 | 1 | 1 |

| | Cpd 27 | Cpd 29 | Cpd 33 | Cpd 37 | Cpd 38 | Cpd 40 |
|---|---|---|---|---|---|---|
| R1 | H | H | $CH_2F$ | $CH_3$ | H | $CH_2CH_3$ |
| R2 | $CH_2CH_3$ | $CH3$ | $C_4H_8N$ | $CH_2CH_3$ | $C_4H_4N$ | $CH_2CH_3$ |
| R2' | $CH_2CH_3$ | $CH_2CH_3$ | n/a | $CH_2CH_2OH$ | n/a | $CH_2CH_3$ |
| R3 | $OCH_3$ | $OCH_2CH_3$ | $OCH_3$ | $OCH_3$ | OH | $OCH_3$ |
| R4 | H | OH | H | H | F | H |
| X = | 1 | 1 | 2 | 2 | 1 | 1 |
| Y = | 2 | 2 | 3 | 1 | 2 | 2 |

FIG. 7

|     | Cpd 43    | Cpd 44   | Cpd 46   | Cpd 48   | Cpd 50   |
|-----|-----------|----------|----------|----------|----------|
| R1  | H         | CH3      | H        | H        | H        |
| R2  | C4H4N     | C5H10N   | C5H10N   | C4H8NO   | CH2CH3   |
| R2' | n/a       | n/a      | n/a      | n/a      | CH2CH3   |
| R3  | CH2COOH   | OCH3     | OCH3     | OCH3     | OCH3     |
| R4  | H         | H        | H        | H        | F        |
| X = | 2         | 1        | 1        | 1        | 1        |
| Y = | 3         | 2        | 2        | 2        | 2        |

R1    methyl, ethyl, propyl, butyl, haloalkyl or hydrogen
R2    methyl, ethyl, propyl, butyl, alkoxy, haloalkyl or hydrogen
R2'    methyl, ethyl, propyl, butyl, alkoxy, haloalkyl or hydrogen
R3    hydroxyl, alkoxy, carboxylic acid or hydrogen
R4    hydrogen, hydroxyl or halogen
X =    (CH2) 1,2, or 3
Y =    (CH2) 1,2, or 3

FIG. 7 (continued)

CCL2 INHIBITORS

This application is the National Stage Under 35 U.S.C. § 371 of PCT International Application No. PCT/US2018/037,061 filed on Jun. 12, 2018, which claims priority under 35 USC § 119 of Application No. 62/518,929 filed in the United States of America on Jun. 13, 2017, the entire contents of each of which are hereby incorporated by reference.

FIELD OF THE INVENTION

This invention pertains to inhibitors of the biological activity Monocyte chemoattractant protein-1 (MCP-1, also known as CCL2). The invention provides compounds and methods useful for inhibition of the biological activity of CCL2 and for the treatment of autoimmune, inflammatory, degenerative, proliferative, and metabolic diseases associated with CCL2 and its signaling pathways through the CCR2 G-protein-coupled receptor.

BACKGROUND OF THE INVENTION

Chemokines constitute a family of chemoattractant cytokines and are subdivided into four families on the basis of the number and spacing of the conserved cysteine residues in the N-terminus of the protein. Chemokines play a major role in selectively recruiting monocytes, neutrophils, and lymphocytes, as well as in inducing chemotaxis through the activation of G-protein-coupled receptors. Monocyte chemoattractant protein-1 (MCP-1, also known as CCL2) is one of the key chemokines that regulate migration and infiltration of monocytes/macrophages. CCL2 is a member of the CC chemokine family, which participates in many cellular processes such as chemotaxis [1, 2], cell adhesion [3, 4, 5], trans-endothelial migration (i.e. cellular extravasation) [5, 6], angiogenesis [7, 8], inflammatory response [2, 9, 10], cell proliferation [11] and apoptotic process [12]. CCL2 is produced by many mammalian cell types, including fibroblasts, endothelial, epithelial, smooth muscle, mesangial, astrocytic, monocytic, and microglial cells [2, 13, 14].

CCL2 binds to and transduces signals only through the G-protein-coupled receptor CCR2 to exert its biological activity of altering gene and protein expression, protein phosphorylation and cellular activity. CCR2 is present on many types of mammalian cells including human: peripheral blood mononuclear cells (PBMCs), fibroblasts, vascular smooth muscle cells, endothelial cells and astrocytes. Together, CCL2 and CCR2 constitute the CCL2/CCR2 signaling axis [2, 14, 15, 16, 17, 18, 96]. In addition, CCL2 binds to CCBP2 (CCR9) [16, 19] and DARC receptors [16, 20], which function as decoy receptors and do not transduce signaling cascades [2, 20, 21, 22]. Several important biologic and pathophysiologic processes are activated via the CCL2/CCR2 axis and subsequent signal transduction pathways within mammalian cells which result in alteration of gene and protein expression, phosphorylation and cellular function.

Upon CCL2 binding to CCR2 the receptor complex initiates signal transduction and activates heterotrimeric Gi-protein consisting of G-protein alpha-i family subunit and G-protein beta/gamma subunit [23, 24]. After CCR2 activation G-protein beta/gamma dissociates from G-protein alpha-i family [24, 25]. CCR2 via Gi-protein activates several PI3K (Phosphoinositide 3-kinase) isoforms, for example, PI3K reg class IA (p85) and PI3K class II (CII-alpha) [4, 26, 27]. PI3K reg class IA (p85) forms heterodimer with catalytic subunit PI3K cat class IA (p110-delta) [5, 28, 29]. Activated PI3K catalyzes transformation of PtdIns (4,5)P2 (Phosphatidylinositol 4,5-bisphosphate) to PtdIns(3,4,5)P3 [30], [31]. PtdIns(3,4,5)P3, in turn, activates CDC42 (cell division control protein 42 homolog) [5, 32] and Rac1 (i.e. Ras-related C3 botulinum toxin substrate 1) [5] via unknown guanine exchange factors (GEFs) [30, 31, 33]. CDC42 and, probably, Rac1 bind to WASP (Wiskott-Aldrich syndrome protein), which, in turn, activates Arp2/3 complex to promote Actin cytoskeletal polymerization resulting in cytoskeleton remodeling [13, 34, 35]. The CCL2-induced cytoskeleton remodeling is important for activation of alpha-4/beta-1 integrin, alpha-5/beta-1 integrin, alpha-M/beta-2 integrin and alpha-L/beta-2 integrin, which participate in cellular adhesion and trans-endothelial migration (i.e. cellular extravasation of leukocytes from blood vessels into the surrounding tissues) [3, 5, 6, 17, 32, 35, 36, 37, 96]. 40]. CCL2 also induces increase in blood-brain barrier permeability. This process is accompanied by phosphorylation and redistribution of tight junction (TJ) proteins [41, 42, 43, 44, 45]. CCL2 decreases gene expression and protein levels of Caveolin-1 and TJ proteins ZO-1, ZO-2, Claudin-5 and Occludin [42, 43]. Downregulation of Caveolin-1 results in redistribution of ZO-1 and Occludin [46]. Moreover, CCL2 induces TJ remodeling via Caveolin-1-mediated internalization of Occludin and Claudin-5 [47]. In addition, CCL2 induces redistribution of Claudin-5, ZO-1, ZO-2 and Occludin via a RhoA/PKC-alpha- and PKC-zeta-dependent mechanism. Redistribution of TJ proteins results in increase of blood-brain barrier permeability enabling leukocyte extravasation into the central nervous system [41, 45, 48].

CCL2 binding to CCR2 also activates ERK1/2 (also known as mitogen-activated protein kinase 3 or MAPK3) via a different signal transduction pathway [2, 24, 49, 50]. ERK1/2 up-regulates gene expression and phosphorylates transcription factor ETS-1, which in turn induces gene expression of ITGB3 (Integrin subunit beta 3), which is important for angiogenesis [51, 52, 53]. CCL2 also stimulates expression of MMP-2 (Matrix metalloproteinase-2) in an ERK1/2-dependent manner, which is essential for trans-endothelial migration of leukocytes [54]. ERK1/2 stimulates activation of transcription factor AP-1, consisting of c-Fos and c-Jun (c-Jun/c-Fos heterodimer) [11, 55, 56]. CCL2-induced activation of AP-1 is essential for cell proliferation [11]. In addition, CCL2-induced AP-1 activates expression of iNOS (Inducible nitric oxide synthase) [57, 58, 59]. CCL2 induces the activation of NF-kB in an ERK1/2- and PI3K/AKT-dependent manner [18]. NF-kB in turn up-regulates expression of ICAM-1 (Intercellular Adhesion Molecule 1, also known as CD54), which is the most important protein for cell adhesion [9, 60, 61]. Thus, CCL2 biological activity is critical for the process of cellular adhesion and subsequent leukocyte extravasation into tissues and organs.

In addition, CCL2 binding to CCR2 induces expression of cytokines; IL-1 alpha (Interleukin 1 alpha) and IL-1 beta (Interleukin 1 beta) [10, 62, 63, 64, 65] and IFN-gamma (Interferon gamma) [10], probably, via NF-kB [10, 64, 66]. Both AP-1 and NF-kB activate expression of other pro-inflammatory cytokines such as; IL-1b (Interleukin 1 beta), IL-6 (Interleukin 6) and, TNF-alpha (Tumor necrosis factor alpha) from target cells [9, 10, 11, 60, 62, 65, 66, 67] which participate in increasing inflammatory response and contribute to tissue damage, pain and loss of function in several inflammatory diseases.

CCL2 binding to CCR2 up-regulates expression of transcription factor MCPIP [68]. MCPIP increases expression of transcription factor HIF1A [69]. In addition, HIF1A is activated by ERK1/2 phosphorylation [7, 70]. HIF1A increases gene and protein expression of VEGF-A (Vascular endothelial growth factor A), which is critical for angiogenesis [69]. Furthermore, MCPIP up-regulates expression of other proteins such as; Cadherin 12, CDH19 and VE-cadherin which participate in CCL2-induced angiogenesis as well [68]. Moreover, MCPIP increases in expression of iNOS [71, 72] and activates p47-phox [71, 72, 73], thus contributing to reactive oxygen species generation, oxidative stress which also induces the process of angiogenesis [71, 72, 73, 74, 75, 76]. Lastly, CCL2-induced actin filament polymerization also contributes to dimerization and activation of MMP-14 (Matrix metalloproteinase-14), which is essential for angiogenesis [38, 39,] Angiogenesis can be a normal process; however in some circumstances it can contribute to disease pathogenesis such as in cancer and diabetes. Thus, CCL2 biological activity is essential in driving the process of angiogenesis in several disorders.

Increases in the blood levels of CCL2 and biological activity of the CCL2/CCR2 axis signal transduction pathway are associated with many disorders and diseases such as but not limited to: Asthma, Behcet syndrome, Bronchitis, Cancer, Coronary Artery Disease, Dermatitis, Glomerulonephritis, Hepatitis, Multiple sclerosis, Pancreatitis, Psoriasis, Pulmonary fibrosis, Restenosis, Rheumatoid arthritis, Scleroderma, Sjogren syndrome, Systemic Lupus Erythematosus, Uveitis and others [77, 78, 79, 80, 81, 82, 83, 84, 85, 86, 87, 88, 89, 90, 91, 92, 93, 94, 95].

SUMMARY OF THE INVENTION

According to one embodiment of the present invention, there is provided a compound of Formula 1 below:

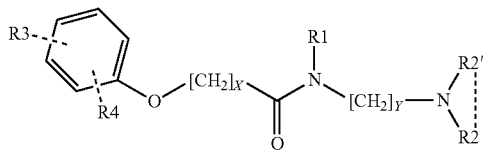

wherein:
R1 is independently selected from methyl, ethyl, propyl, butyl, haloalkyl, or hydrogen;
R2 and R2' are independently selected from methyl, ethyl, propyl, butyl, alkoxy, haloalkyl, or hydrogen. Alternatively, R2 and R2' are fused into a heterocyclic ring with 5 or 6 members;
R3 is independently selected from hydroxyl, alkoxy, carboxylic acid, haloalkyl, halogen, or hydrogen;
R4 is independently selected from hydrogen, hydroxyl, or halogen;
X is 1-3;
Y is 1-3;
or a pharmaceutically acceptable salt, addition compound, or pro-drug thereof.

According to another embodiment of the present invention, there is provided a compound of Formula 2 below:

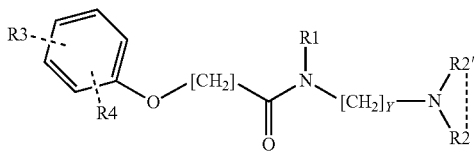

wherein:
R1 is independently selected from methyl, ethyl, or hydrogen;
R2 and R2' are independently selected from methyl, ethyl, n-propyl, 2-propyl, tert-butyl, alkoxy, or hydrogen;
R3 is independently selected from methyl, ethyl, hydroxyl, carboxylic acid, alkoxy, halogen or hydrogen;
R4 is independently selected from hydrogen, hydroxyl or halogen;
Y is 1-3;
or a pharmaceutically acceptable salt, addition compound, or pro-drug thereof.

Additional embodiments of the invention include a pharmaceutical composition comprising a compound as defined above and a pharmaceutically acceptable carrier and/or diluent therefor.

Another embodiment of the invention is the inhibition of the biological activity of CCL2 and the CCL2/CCR2 signaling pathway in mammalian cells.

Still another embodiment of the invention is the inhibition of the production by mammalian cells of at least one pro-angiogenic protein induced by CCL2.

Yet another embodiment of the invention is inhibition of the production by mammalian cells of at least one pro-inflammatory cytokine induced by CCL2.

An additional embodiment of the invention in the inhibition of the production by mammalian cells of at least one protein that promotes cellular adhesion and/or trans-endothelial migration of leukocytes in mammalian tissues.

A further embodiment of the invention is the use of a compound as defined above in the manufacture of a medicament for the treatment of a mammal at risk for or having at least one disease or disorder associated with increased biological activity CCL2 acting through its interaction with the CCR2 receptor. Non-limiting examples of such disorders are: autoimmune diseases; inflammatory diseases; auto-inflammatory conditions; pain conditions; respiratory ailments; airway and pulmonary conditions; gastrointestinal disorders; allergic diseases; atopic disorders, infection-based diseases; trauma and tissue injury-based conditions; fibrotic diseases; ophthalmic/ocular diseases; joint, muscle, and bone disorders; skin/dermatological diseases; renal diseases; genetic diseases; hematopoietic diseases; liver diseases; oral diseases; metabolic diseases, including diabetes (e.g. Type II) and complications thereof; proliferative diseases; cardiovascular conditions; vascular conditions including restenosis; neuro-inflammatory conditions; neurodegenerative conditions; cancer; and pulmonary conditions.

One embodiment of the invention is directed to a method of treating a mammal at risk for or having a disease or disorder mediated by a pro-inflammatory cytokine induced by CCL2 through its interaction with CCR2; comprising administering to a subject an amount of a compound as described herein for the treatment of a disease or disorder. Inflammatory diseases and disorders associated with CCL2 induced pro-inflammatory cytokines include, but are not limited to: autoimmune diseases; inflammatory diseases; auto-inflammatory conditions; pain conditions; respiratory ailments; airway and pulmonary conditions; gastrointestinal disorders; allergic diseases; atopic disorders; fibrotic diseases; ophthalmic/ocular diseases; joint, muscle and bone disorders; skin/dermatological diseases; renal diseases; genetic diseases; hematopoietic diseases; liver diseases; oral diseases; metabolic diseases, including diabetes (e.g. Type II) and complications thereof; proliferative diseases; cardiovascular conditions; vascular conditions; neuro-inflammatory conditions; neurodegenerative conditions; cancer; and pulmonary disorders.

Another embodiment of the invention is directed to a method of treating a subject at risk for or having a disease or disorder associated with abnormal angiogenesis mediated by CCL2 through its interaction with CCR2 comprising administering to a subject an amount of a compound as described herein for the treatment of a disease or disorder. Diseases and disorders associated with abnormal angiogenesis include, but are not limited to: vascular tumors, arteriosclerosis, retinopathy, invasive and metastatic cancers.

Yet another embodiment of the invention is a compound that inhibits the biological activity of the CCL2/CCR2 axis signal transduction cascade by simultaneously decreasing the intracellular levels of other components of these pathways that are increased due to CCL2 binding to CCR2.

BRIEF DESCRIPTIONS OF THE DRAWINGS

FIG. 1A-D: shows that treatment with compounds of the invention reduces expression of IL-6 (FIG. 1A), TNF-alpha (FIG. 1B), IFN-gamma (FIG. 1C) and IL-1a (FIG. 1D) which are upregulated by CCL2 in freshly isolated human PBMC cells. Culture supernatant was diluted in some cases for quantitation of cytokine levels.

Figure 2:
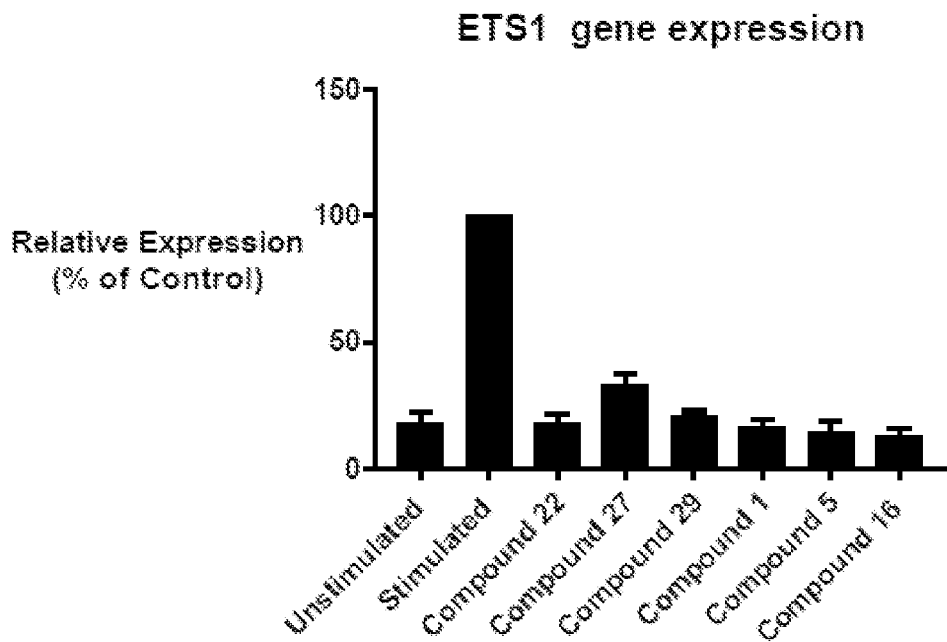

FIG. 2: shows that treatment with compounds of the invention decreases expression of ETS1 gene that is upregulated by CCL2 in CD4+ T cells.

Figure 3:
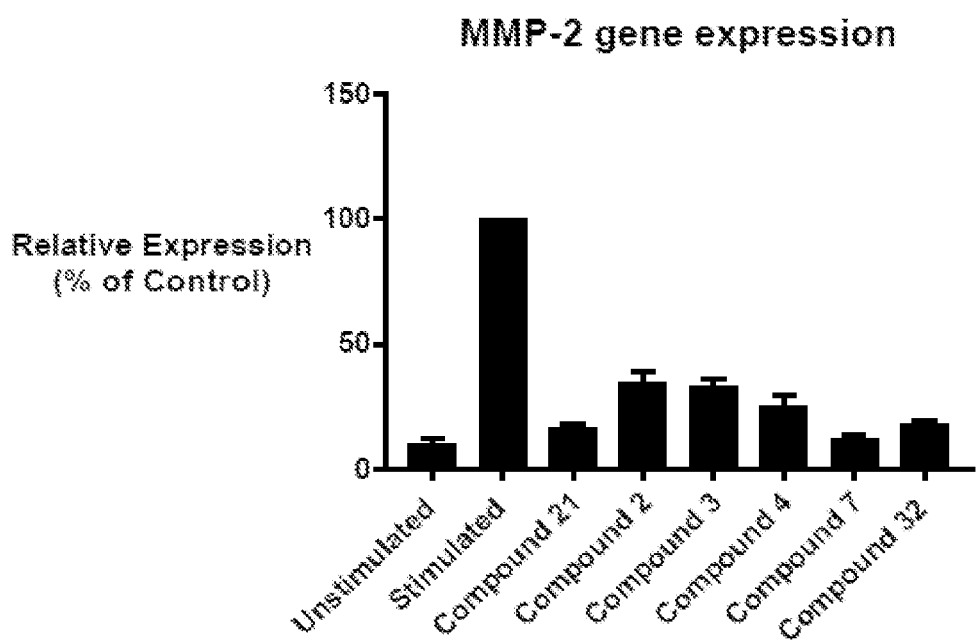

FIG. 3: shows that treatment with compounds of the invention reduces MMP-2 expression induced by CCL2 in human endothelial cells.

Figure 4A:
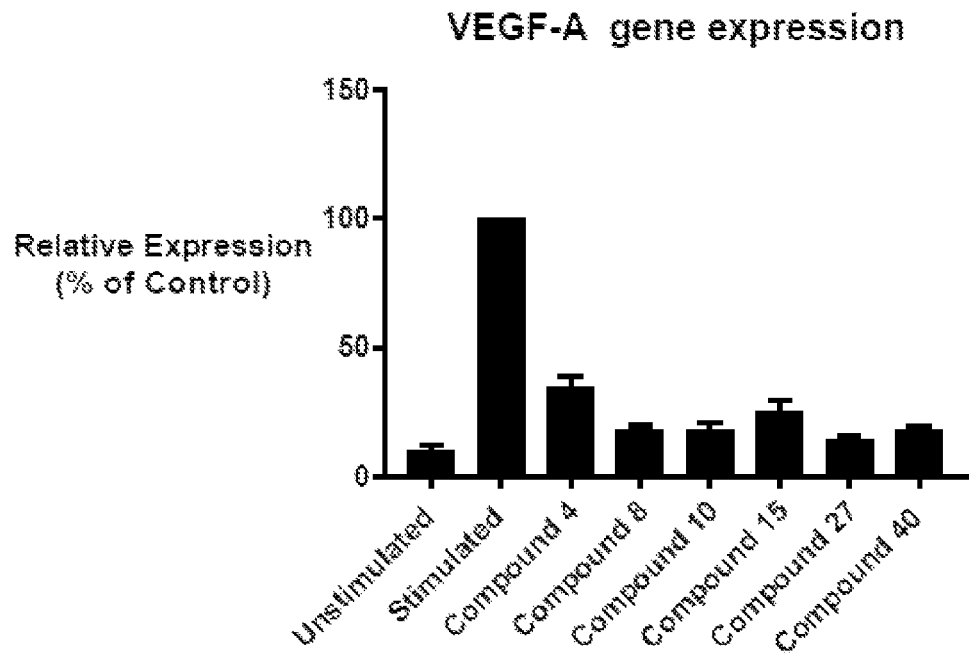
Figure 4B:
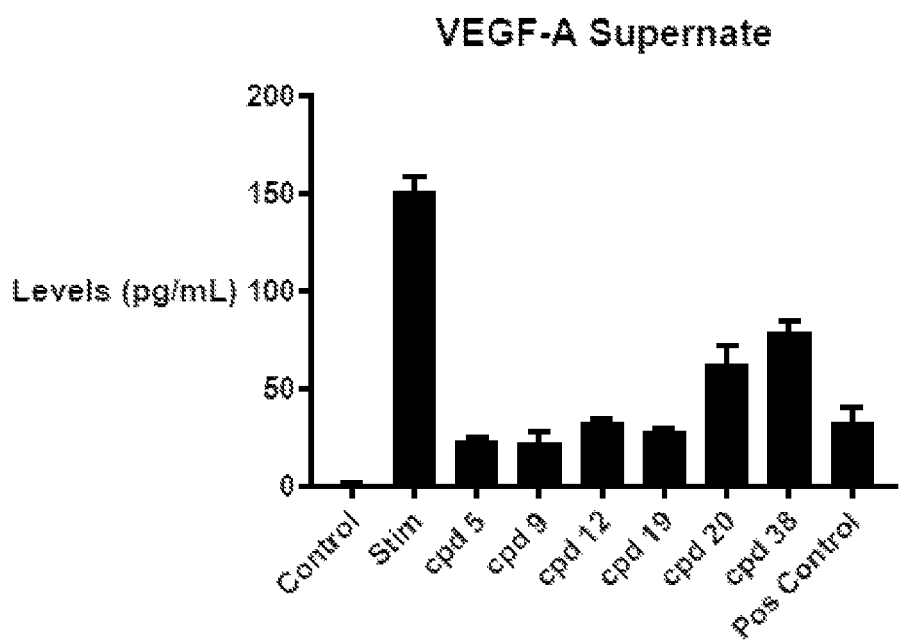

FIG. 4A and 4B: shows that treatment with compounds of the invention reduces CCL2 induced VEGF-A production in human fibroblast cells. FIG. 4A: VEGF-A gene expression; FIG. 4B: VEGF-A supernate.

Figure 5A:
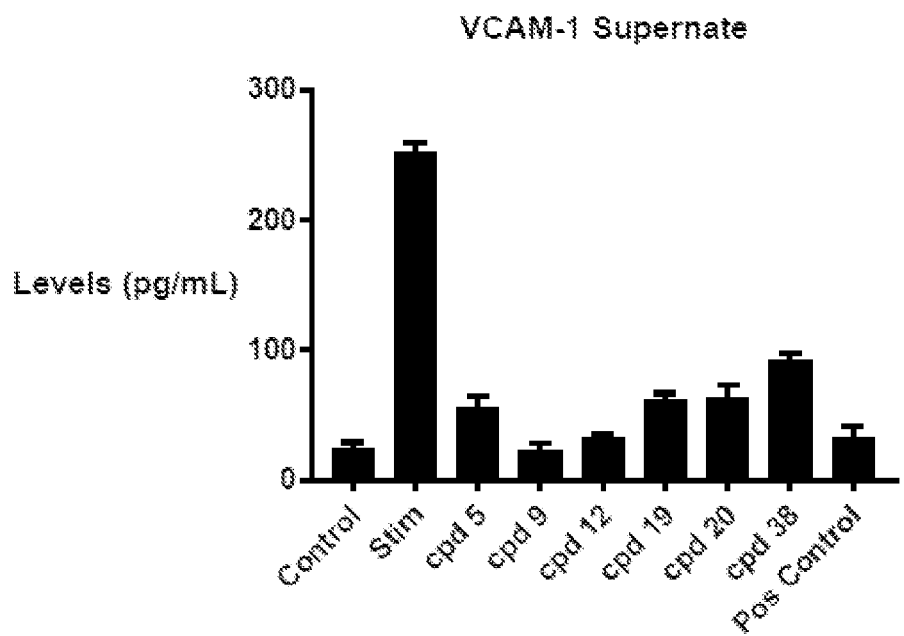
Figure 5B:
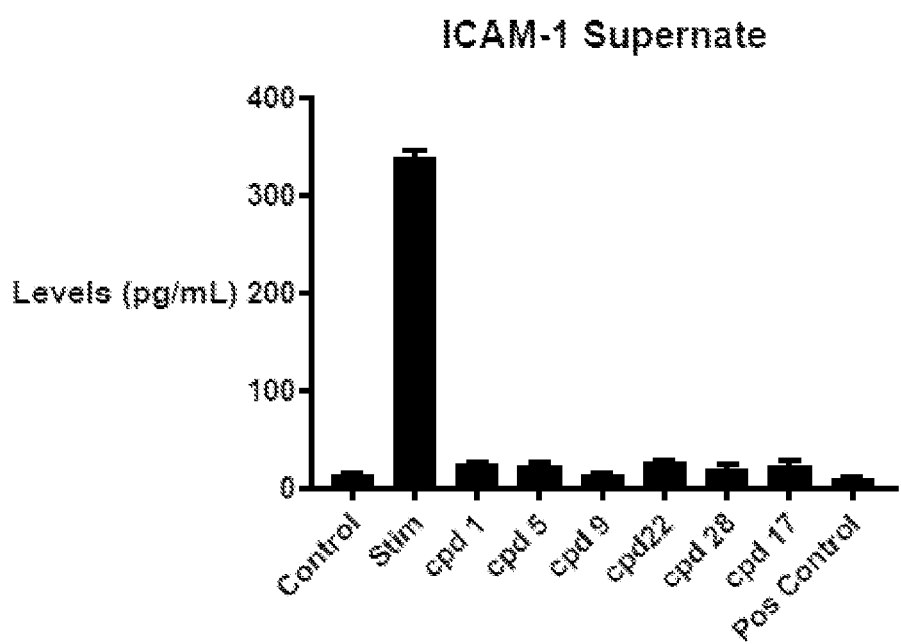

FIG. 5A and 5B: shows that treatment with compounds of the invention reduces CCL2 induced VCAM-1 (FIG. 5A) and ICAM-1 (FIG. 5B) production in endothelial cells.

Figure 6:
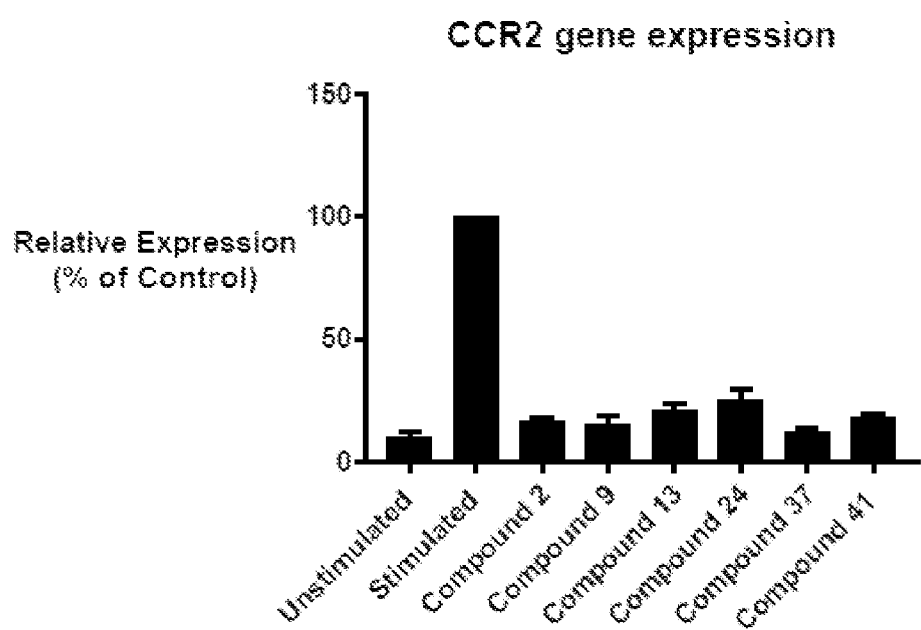

FIG. 6 shows that treatment with compounds of the invention reduces expression of CCR2 gene in CD4+ cells FIG. 7 shows TABLE 1 with various compounds according to Formula 1 and Formula 2.

DETAILED DESCRIPTION OF THE INVENTION

Definitions

"Addition compound" refers to a complex of two or more complete molecules in which each preserves its fundamental structure and no covalent bonds are made or broken (for example, hydrates of salts, adducts).

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl groups include, but are not limited to, methyl, ethyl, n-propyl, 2-propyl, tert-butyl, pentyl, and the like. "Lower alkyl" refers to a straight or branched hydrocarbon containing 1-4 carbon atoms.

"Optionally-substituted alkyl" refers to an alkyl group as defined herein in which one or more hydrogen atom(s) is optionally replaced with a substituent such as halide, hydroxyl, alkoxy, or other heteroatom substituent.

"Alkene" refers to an unsaturated linear divalent hydrocarbon moiety of one to twelve, typically one to six, carbon atoms or a saturated branched divalent hydrocarbon moiety of three to twelve, typically three to six, carbon atoms. Exemplary alkene groups include, but are not limited to, methylene, ethylene, propylene, butylene, pentylene, and the like.

"Alkenyl" refers to a linear monovalent hydrocarbon moiety of two to ten carbon atoms or a branched monovalent hydrocarbon moiety of three to ten carbon atoms, containing at least one C=C double bond, e.g., ethenyl, propenyl, and the like.

"Alkoxy" refers to an alkyl group bonded to an oxygen atom. Alkoxy groups have the general formula: R—O.

"Antagonist" refers to a compound or a composition that attenuates the effect of an agonist. The antagonist can bind reversibly or irreversibly to a region of the receptor in common with an agonist. Antagonist can also bind at a different site on the receptor or an associated ion channel. Moreover, the term "antagonist" also includes functional antagonist or physiological antagonist. Functional antagonist refers to a compound and/or compositions that reverse the effects of an agonist rather than acting at the same receptor, i.e., functional antagonist causes a response in the tissue or animal which opposes the action of an agonist. Examples include agents which have opposing effects on an intracellular second messenger, or, on a physiologic state in an animal (for example, blood pressure). A functional antagonist can sometimes produce responses which closely mimic those of the pharmacological kind.

"Aryl" refers to a monovalent mono-, bi- or tricyclic aromatic hydrocarbon moiety of 6 to 15 ring atoms.

"Optionally-substituted aryl" refers to an aryl group as defined herein in which one or more aryl ring hydrogen is replaced with a non-hydrogen substituent such as halide, alkyl, cyano, hydroxy, alkoxy, etc. When two or more substituents are present in an aryl group, each substituent is independently selected.

"Biological activity" as used herein means having an effect on or eliciting a response from a living cell, tissue, organ or physiologic activity, such as but limited to: altering gene and/or protein expression, protein phosphorylation, cellular behavior or organ function.

"Biomarker" as used herein means a measurable indicator of the severity or the presence of a particular disease state. More generally a biomarker is anything that can be used as an indicator of a particular disease state or some other physiological state of an organism.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its minor image.

"Cycloalkyl" refers to a non-aromatic, typically saturated, monovalent mono-, bi- or tri-cyclic hydrocarbon moiety of three to twenty ring carbons. The cycloalkyl can be optionally substituted with one or more, typically one, two, or three, substituents within the ring structure. When two or more substituents are present in a cycloalkyl group, each substituent is independently selected. Exemplary cycloalkyl groups include, but are not limited to, cyclopropyl, cyclobutyl, cyclopentyl, norbornyl, adamantyl, cyclohexyl, cyclooctyl, etc.

"Derivative" refers to a compound that is derived from some parent compound where one atom is replaced with another atom or group of atoms and usually maintains its general structure. For example, trichlormethane (chloroform) is a derivative of methane.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to: —$CH_2F$, —$CH_2Cl$, —$CF_3$, —$CH_2CF_3$, —$CH_2CCl_3$, and the like.

"Hetero-substituted alkyl" refers to an alkyl group as defined herein that contains one or more heteroatoms such as N, O, or S. Such heteroatoms can be hydroxy, alkoxy, amino, mono- or di-alkyl amino, thiol, alkylthiol, etc.

"Hydroxyalkyl" refers to an alkyl group having one or more hydroxyl substituent(s).

"Enantiomeric excess" refers to the difference between the amounts of enantiomers. The percentage of enantiomeric excess (% ee) can be calculated by subtracting the percentage of one enantiomer from the percentage of the other enantiomer. For example, if the % of (R)-enantiomer is 99% and % of (S)-enantiomer is 1%, the % ee of (R)-isomer is 99%-1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N, O-dimethylhydroxylamino, and the like.

"Ligand" as used herein means a biochemical substance in the form of a nucleic acid, protein or peptide that forms a complex with another biomolecule in a cell or tissue to serve a biological purpose.

"Moderate" as used herein means to decrease the quality, quantity, intensity or duration of a biological product or process.

"Pharmaceutically acceptable excipient" refers to an excipient that is useful in preparing a pharmaceutical composition that is generally safe, non-toxic, and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A "pharmaceutically acceptable salt" of a compound also includes salts formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Pharmaceutically acceptable vehicle means, a carrier or inert medium used as a solvent (or diluent) in which the medicinally active agent is formulated and or administered.

The terms "pro-drug" and "prodrug" are used interchangeably herein and refer to any compound which releases an active parent drug according to Formula I or Formula 2 in vivo when such prodrug is administered to a mammalian subject. Prodrugs of a compound of Formula I or Formula 2 are prepared by modifying one or more functional group(s) present in the compound of Formula I or Formula 2 in such a way that the modification(s) may be cleaved in vivo to release the parent compound. Prodrugs include compounds of Formula I or Formula 2 wherein a hydroxy, amino, or sulfhydryl group in a compound of Formula I or Formula 2 is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I or Formula 2, and the like. For example, the compound according to Formula 1 that is 4-({5-[ethyl(methyl)amino]-3-oxopentyl}oxy)benzoic acid can be reacted with $CH_3CH_2OH$ under acidic conditions to produce: ethyl 4-({5-[ethyl(methyl)amino]-3-oxopentyl}oxy)benzoate, an ester prodrug that will be hydrolyzed to ethanol and the starting compound by esterase enzymes in tissues.

"Pro-inflammatory cytokine" refers to a type of cytokine (i.e. a protein signaling molecule) that is secreted from leukocytes and certain other cell types that promote inflammation by their biological effect on other cells and tissue in mammalian organisms. Non limiting examples of pro-inflammatory cytokines are: Interleukin 1 (IL-1; IL-1a & IL-1b), Interleukin 6 (IL-6), Interleukin 13 (IL-13), Tumor Necrosis Factor alpha (TNF-alpha), Interferon gamma (IFN-gamma) and Interleukin 8 (IL-8).

"Protecting group" refers to a moiety, except alkyl groups, that when attached to a reactive group in a molecule masks, reduces or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P, or S) to which it is attached.

"Signal transduction" or "signaling pathway activity" refers to a biochemical causal relationship generally initiated by a protein-protein interaction such as binding of a biological active factor to a receptor, resulting in transmission of a signal from one portion of a cell to another portion of a cell. In general, the transmission can involve specific phosphorylation of one or more tyrosine, serine, or threonine residues on one or more protein components such as enzymes or transcription factors (i.e. intracellular secondary messengers) in the series of reactions causing signal transduction (often referred to as a cascade) that results in measurable changes to the cell. Penultimate cellular processes typically include nuclear events, resulting in a change in gene expression. Terminal events of signal transduction cascade result in changes in cellular activity such as but not limited to: alterations in protein products produced and/or secreted by the cell, changes in cellular behavior characteristics of division, motility, adherence, etc.

"Stereoisomer" means molecules that have the same molecular formula and sequence of bonded atoms (constitution), but differ in the three-dimensional orientations of their atoms in space. By definition, molecules that are stereoisomers of each other represent the same structural isomer. The chemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

"A therapeutically effective amount" means the amount of a compound that, when administered to an individual for treating a disease, is sufficient to effect such treatment for the disease. The "therapeutically effective amount" will vary depending on the compound, the disease and its severity or affected organ or tissue and the age, weight, etc., of the individual to be treated.

"Tautomer" or "tautomeric form" means structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. The compounds of the present invention according to Formula 1 and Formula 2 can exist in different tautomer depend on the environment of the particular compound such as the acidity or alkalinity (i.e. pH) of the solution in which they are dissolved.

"Treating" or "treatment" of a disease means inhibiting the disease, i.e., arresting or reducing the pathophysiologic process or processes of the disease or its clinical symptoms; or relieving the disease, i.e., causing regression of the pathophysiologic process or processes of disease or reducing the clinical manifestations of the pathophysiologic process or processes of the specific disease.

I. METHODS OF SYNTHESIS

The compounds of Formula I or Formula 2 may be prepared by the methods described below, together with synthetic methods known in the art of organic chemistry, or modifications and transformations that are familiar to those of ordinary skill in the art. The starting materials used herein are commercially available or may be prepared by routine methods known in the art, such as those methods disclosed in standard reference books such as the Compendium of Organic Synthetic Methods, Vol. I-XII (eds. John Wiley & Sons, Inc., Hoboken, N.J., 2009). Preferred methods include, but are not limited to, those described below.

Preparation of the example compounds of Table 1 were prepared with standard procedures well known to those skilled in the art as follows:

All synthetic chemistry was performed in standard laboratory glassware unless indicated otherwise in the examples. Commercial reagents were used as received from the manufacturer. Analytical LC/MS was performed on an Agilent 1200 system with a variable wavelength detector and Agilent 6140 single quadrupole mass spectrometer, alternating positive and negative ion scans. Retention times were determined from the extracted 220 nm UV chromatogram. Preparative HPLC was performed on a Wufeng LC120 system (Shanghai Wufeng Scientific Instruments Co., Ltd. Shanghai., China). 1H NMR was performed on a Bruker AVANCE™ 300 at 300 MHz or a Bruker AVANCE™ DRX 500 at 500 MHz. For complicated splitting patterns, the apparent splitting is tabulated. Analytical thin layer chromatography was performed on silica (Macherey-Nagel ALUGRAM® Xtra SIL G, 0.2 mm, UV254 indicator) and was visualized under UV light. Silica gel chromatography was performed manually, or with an Isco COMBIFLASH® for gradient elutions.

Analytical LC/MS method: HPLC column: Kinetex, 2.6 μm, C18, 50×2.1 mm, maintained at 40° C. HPLC Gradient: 1.0 mL/min, 95:5:0.1 water:acetonitrile:formic acid to 5:95:0.1 water:acetonitrile:formic acid in 2.0 min, maintaining for 0.5 min. Preparative HPLC method: HPLC Gradient: 100 mL/min, 95:5:0.1 acetonitrile:water:trifluoroacetic acid to 70:30:0.1 acetonitrile:water:trifluoroacetic acid in 9.5 min, maintaining for 0.5 min.

Compound 1: 4-[3-[2-(Dimethylamino)ethylamino]-3-oxopropoxy]benzoic Acid

A solution of 3-(4-(methoxycarbonyl)phenoxy)propanoic acid (150 mg, 0.67 mmol) in thionyl chloride (750 μL, 10.32 mmol) was stirred at 50° C. for 1 h. The reaction mixture was concentrated under a nitrogen stream to remove thionyl chloride. The residue was dissolved in chloroform (1 mL) and evaporated under a nitrogen stream. The residue was dissolved in chloroform (1 mL) and added dropwise to a stirred solution of N,N-dimethylethylenediamine (66 μL, 0.60 mmol) in chloroform (1 mL) at room temperature. The reaction mixture was stirred at room temperature for 18 h. The reaction mixture was washed with saturated sodium bicarbonate (1 mL). The aqueous layer was extracted with chloroform (1 mL). The combined organic layers were dried over sodium sulfate and evaporated to give Methyl 4-[3-[2-(dimethylamino)ethylamino]-3-oxopropoxy]benzoate (107 mg, 55%) as a white crystalline solid. Next, A mixture of methyl 4-(3-((2-(dimethylamino)ethyl)amino)-3-oxopropoxy)benzoate (173 mg, 0.59 mmol) and lithium hydroxide (1 N aqueous solution, 865 μL, 865 mmol) in 1,4-dioxane (865 μL) was stirred at room temperature for 1 h. The reaction mixture was neutralized to pH 7 by addition of acetic acid. The mixture was concentrated to 1 mL, washed with chloroform (1 mL) and evaporated. The crude product was purified by preparative HPLC. The pure fractions were combined and lyophilized. The residue was dissolved in water (20 mL) and to this solution was added 1 N hydrochloric acid (500 μL). The solution was evaporated. The residue was dissolved in water (3×10 mL) and evaporated. The residue was dissolved in water (5 mL) and lyophilized to yield Compound 1: 4-[3-[2-(Dimethylamino)ethylamino]-3-oxopropoxy]benzoic acid (45 mg, 24%) as a white crystalline solid.

LCMS: 99%, tR=0.243 min, m/z=281 [M+H]+, Method: BB_LCMS_05_KINETEX.
1H NMR (300 MHz, DMSO-d6) δ 12.61 (br s, 1H), 10.24 (br s, 1H), 8.48-8.32 (m, 1H), 7.88 (d, J=8.8 Hz, 2H), 7.00

(d, J=8.9 Hz, 2H), 4.28 (t, J=6.1 Hz, 2H), 3.52-3.40 (m, 2H), 3.19-3.07 (m, 2H), 2.77 (s, 6H), 2.63 (t, J=6.1 Hz, 2H).

Compound 7: N-[2-(Diethylamino)ethyl]-3-(4-methoxyphenoxy)propanamide

A mixture of 3-(4-methoxyphenoxy)propanoic acid (100 mg, 0.51 mmol) in thionyl chloride (500 μL, 6.88 mmol) was stirred at room temperature for 1.5 h. The reaction mixture was concentrated under a nitrogen stream to remove thionyl chloride. The residue was dissolved in chloroform (1 mL) and evaporated under a nitrogen stream. The residue was dissolved in chloroform (1 mL) and added dropwise to a stirred solution of N,N-diethylethylenediamine (66 μL, 0.46 mmol) in chloroform (1 mL) at room temperature. The reaction mixture was stirred at room temperature for 30 min. The mixture was washed with saturated sodium bicarbonate (1 mL). The aqueous layer was extracted with chloroform (1 mL) and the combined organic layers were dried over sodium sulfate and evaporated. The crude product (108 mg) was dissolved in 1 N hydrochloric acid (5 mL) and the aqueous layer was washed with diethyl ether (5 mL). The aqueous layer was made basic to pH 8 by addition of sodium bicarbonate and extracted with diethyl ether (5 mL). The organic layer was dried over sodium sulfate and evaporated to give Compound 7: N-[2-(diethylamino)ethyl]-3-(4-methoxyphenoxy)propanamide (89 mg, 59%) as a pale yellow oil.

LCMS: 99%, tR=0.728 min, m/z=295 [M+H]+, Method: BB_LCMS_05_KINETEX. 1H NMR (300 MHz, DMSO-d6) δ 7.84 (t, J=5.7 Hz, 1H), 6.87-6.80 (m, 4H), 4.09 (t, J=6.2 Hz, 2H), 3.69 (s, 3H), 3.16-3.06 (m, 2H), 2.53-2.38 (m, 8H), 0.94 (t, J=7.1 Hz, 6H).

Compound 12: N-[2-(Diethylamino)ethyl]-N-ethyl-3-(4-methoxyphenoxy)propanamide

N-[2-(Diethylamino)ethyl]-N-ethyl-3-(4-methoxyphenoxy)propanamide was prepared by the method used for compound 7 above, starting with 3-(4-methoxyphenoxy)propanoic acid and N,N,N'-triethylenediamine.
LCMS: 99%, tR=0.976 min, m/z=323 [M+H]+, Method: BB_LCMS_05_KINETEX.
1H NMR (300 MHz, Chloroform-d) δ 6.90-6.80 (m, 4H), 4.33-4.25 (m, 2H), 3.78 (s, 3H), 3.51-3.33 (m, 4H), 2.81 (t, J=6.7 Hz, 2H), 2.68-2.50 (m, 6H), 1.22 (t, J=7.1 Hz, 3H), 1.06 (t, J=7.3 Hz, 6H).

Compound 16: 3-(4-Methoxyphenoxy)-N-[2-(morpholin-4-yl)ethyl]propanamide 3-(4-Methoxyphenoxy)-N-[2-(morpholin-4-yl)ethyl]propanamide was prepared by the method used for compound 7 above, starting with 3-(4-methoxyphenoxy)propanoic acid and 2-morpholinoethanamine.
LCMS: 98%, tR=0.444 min, m/z=309 [M+H]+, Method: BB_LCMS_05_KINETEX.
1H NMR (300 MHz, DMSO-d6) δ 7.88 (t, J=5.7 Hz, 1H), 6.88-6.80 (m, 4H), 4.09 (t, J=6.2 Hz, 2H), 3.69 (s, 3H), 3.60-3.49 (m, 4H), 3.24-3.13 (m, 2H), 2.53-2.44 (m, 2H), 2.42-2.29 (m, 6H).

Compound 17: N-[2-(Diethylamino)ethyl]-3-(3-fluoro-4-methoxyphenoxy)propanamide

A mixture of 3-fluoro-4-methoxyphenol (250 mg, 1.76 mmol), acrylonitrile (1.2 mL, 17.6 mmol), potassium carbonate (12 mg, 0.09 mmol) and tert-butanol (17 μL, 0.18 mmol) was stirred at 75° C. for 16 h in a sealed tube. To the reaction mixture was added potassium carbonate (12 mg, 0.09 mmol) and the stirring was continued at 75° C. for 8 h. The reaction mixture was evaporated. The residue was taken up in toluene (2 mL) and washed with 10% aqueous sodium hydroxide (1 mL). The aqueous layer was extracted with toluene (2 mL). The combined organic layers were washed with 10% aqueous potassium bisulfate (1 mL), dried over sodium sulfate and evaporated to give 3-(3-fluoro-4-methoxyphenoxy)propanenitrile (231 mg, 67%) as an off-white solid. Next, a mixture of 3-(3-fluoro-4-methoxyphenoxy)propanenitrile (222 mg, 1.14 mmol) in concentrated hydrochloric acid (1 mL) and water (500 μL) was stirred at 100° C. for 3 h. The reaction mixture was poured onto ice (5 g) and the mixture was stirred for 15 min. The precipitate was collected, washed with water (2 mL) and dried in air. The crude product (196 mg) was dissolved in 10% aqueous sodium carbonate (10 mL) and the aqueous layer was washed with dichloromethane (10 mL). The aqueous layer was acidified to pH 1 by addition of 1 N hydrochloric acid. The precipitate was collected, washed with water (2×1 mL) and dried in air to give 3-(3-Fluoro-4-methoxyphenoxy)propanoic acid (103 mg, 42%) as an off-white solid. Finally, a mixture of 3-(3-Fluoro-4-methoxyphenoxy)propanoic acid (100 mg, 0.51 mmol) in thionyl chloride (500 μL, 6.88 mmol) was stirred at room temperature for 1.5 h. The reaction mixture was concentrated under a nitrogen stream to remove thionyl chloride. The residue was dissolved in chloroform (1 mL) and evaporated under a nitrogen stream. The residue was dissolved in chloroform (1 mL) and added dropwise to a stirred solution of N,N-diethylethylenediamine (66 μL, 0.46 mmol) in chloroform (1 mL) at room temperature. The reaction mixture was stirred at room temperature for 30 min. The mixture was washed with saturated sodium bicarbonate (1 mL). The aqueous layer was extracted with chloroform (1 mL) and the combined organic layers were dried over sodium sulfate and evaporated. The crude product (108 mg) was dissolved in 1 N hydrochloric acid (5 mL) and the aqueous layer was washed with diethyl ether (5 mL). The aqueous layer was made basic to pH 8 by addition of sodium bicarbonate and extracted with diethyl ether (5 mL). The organic layer was dried over sodium sulfate and evaporated to give Compound 17: N-[2-(diethylamino)ethyl]-3-(3-fluoro-4-methoxyphenoxy)propanamide (54 mg, 59%) as a pale yellow oil.

1H NMR (300 MHz, Chloroform-d) δ 6.89 (t, J=9.2 Hz, 1H), 6.73 (dd, J=12.6, 2.9 Hz, 1H), 6.67-6.60 (m, 1H), 6.67-6.56 (m, 1H), 4.21 (t, J=6.0 Hz, 2H), 3.86 (s, 3H), 3.40-3.30 (m, 2H), 2.66 (t, J=6.0 Hz, 2H), 2.61-2.51 (m, 6H), 1.03 (t, J=7.1 Hz, 6H).

II. METHODS OF INHIBITION

The compounds and compositions described herein inhibit the biological activity of the CCL2 induced through its binding to CCR2 and subsequent CCL2/CCR2 axis mediated signal transduction in cells and tissues. This is thought to occur by moderation or modification of protein components of the associated signal transduction pathways or inhibition of their production by decreasing expression of their mRNA precursors. In addition to inhibiting the transduction of biochemical signals in cells or tissues caused by the interaction of CCL2 and its CCR2 ligand, the compounds and compositions described also moderate later portions of associated pathophysiological process. Here, this is thought to occur by either decreasing the genetic expression of relevant ligands, protein kinases, and transcription factors or by moderating the physical and/or the chemical interactions of the relevant ligands involved to reduce the cellular activity induced by CCL2 through its interaction with the CCL2 receptor. Non-limiting examples are: down-regulation of ETS-1 (also known as, V-ets erythroblastosis virus E26 oncogene homolog 1) gene expression, inhibition of expression of iNOS, reducing the physical association of two ligands with each other such as dimerization and activation of MMP-14, and remarkably the inhibition of the expression of the CCL2 G-protein-coupled receptor CCR2 itself.

The compounds and compositions described are also useful for inhibiting production and/or secretion by target cells of proteins capable of inducing; inflammation, induced by CCL2. Non limiting examples are inhibition of secretion or inhibition of production of INF-gamma, TNF-alpha, IL-1a and IL-6.

In addition, the compounds and compositions described are useful in moderating CCL2 induced angiogenesis, leukocyte adhesion and cellular migration through reduction of the production of proteins that are critical to these processes such as, but not limited to; ITGB3, VEGF-A and ICAM-1.

III. METHODS OF TREATMENT

Because CCL2 is involved in the pro-inflammation response, angiogenesis, leukocyte adhesion and extravasation, and because it acts as a cytokine when secreted by cells, inhibition of CCL2/CCR2 signaling pathways expression and activity has implications for treatment of many disorders with diverse etiologies. Increased tissue or blood levels of CCL2 through its interaction with the CCR2 receptor and subsequent downstream signal transduction pathways is directly contributory to the pathogenesis of: autoimmune diseases; inflammatory diseases; auto-inflammatory conditions; pain conditions; respiratory ailments; airway and pulmonary conditions; gastrointestinal disorders; allergic diseases; atopic disorders, infection-based diseases; trauma and tissue injury-based conditions; fibrotic diseases; ophthalmic/ocular diseases; joint, muscle, and bone disorders; skin/dermatological diseases; renal diseases; genetic diseases; hematopoietic diseases; liver diseases; oral diseases; metabolic diseases, including diabetes (e.g. Type II) and complications thereof; proliferative diseases; cardiovascular conditions; vascular conditions including restenosis; neuro-inflammatory conditions; neurodegenerative conditions; cancer; and pulmonary conditions.

CCL2 increases the levels of secreted pro-inflammatory cytokines and chemokines through its interaction with CCR2 receptor and subsequent downstream signaling pathway effects such as, but not limited to: IL-1 beta, TNF-alpha, IL-6, and IFN-gamma. These increased pro-inflammatory cytokines and chemokines induce the pathogenic processes responsible for acute and chronic diseases and their complications such as, but not limited to; Atopic disorders, Autoimmune diseases, Carcinoma, Cardiac disorders, Dermatologic diseases, Fibrosis, Gastrointestinal disorders, Hepatic diseases, Infectious diseases, Inflammatory disorders, Metabolic disorders (e.g. diabetes), Nephropathies, Neoplasia, Neurodegenerative disorders, Ophthalmologic disorders, Osteoporosis, Pulmonary diseases, Vascular conditions including restenosis, and others. Inhibition of the biological activity of CCL2 via CCL2/CCR2 axis signal transduction by the compounds of the present invention reduces the levels of these pro-inflammatory cytokines and chemokines.

CCL2 through its interaction with CCR2 receptor also upregulates the expression of genes that produce intracellular intermediate ligands such as, but not limited to: protein kinases, transcription factors, G-Protein Coupled Receptors (GPCRs), and other biological ligands important to downstream initiation and/or maintenance of pathogenic processes such as; inflammation, angiogenesis, leukocyte adherence and extravasation. Examples, of genes affected by the CCL2 signal transduction that are known to be upregulated include, but are not limited to: MAPK3 (Entrez Gene: 5594 & 5595), MCPIP (Entrez Gene: 80149) and ETS-1 (Entrez Gene: 2113). Up regulation and increased expression of these intracellular intermediate ligands lead to pathogenesis responsible for acute and chronic diseases and their complications such as, but not limited to; Atopic disorders, Autoimmune diseases, Carcinoma, Cardiac disorders, Dermatologic diseases, Fibrosis, Gastrointestinal disorders, Hepatic diseases, Infectious diseases, Inflammatory disorders, Metabolic disorders (e.g. diabetes), Nephropathies, Neoplasia, Neurodegenerative disorders, Ophthalmologic disorders, Osteoporosis, Pulmonary diseases, Vascular conditions including restenosis, and others. Inhibition of the biological activity of CCL2 via CCL2/CCR2 axis signal transduction by the compounds of the present invention reduces the level of expression of these intracellular intermediate ligands.

The biological activity of CCL2 acting through its binding to the CCR2 receptor also induces increases in gene expression and presence of structural cellular proteins that critical are to downstream initiation and/or maintenance of pathogenic processes such as; inflammation, angiogenesis, leukocyte adherence and extravasation. Examples, of structural cellular proteins known to be upregulated by the CCL2 signal transduction include, but are not limited to: ICAM-1, MMP-2 and VEGF-A, Up regulation and increased expression of these structural cellular proteins lead to pathogenesis responsible for acute and chronic diseases and their complications such as but not limited to; Atopic disorders, Autoimmune diseases, Carcinoma, Dermatologic diseases, Fibrosis, Gastrointestinal disorders, Hepatic diseases, Inflammatory diseases, Nephropathy, Neoplasia, Neurodegenerative disorders, Ophthalmologic disorders, Osteoporosis, Pulmonary Disease and others. Inhibition of the biological activity of CCL2 via CCL2/CCR2 axis signal transduction by the compounds of the present invention reduces the level of expression of these structural cellular proteins.

In an embodiment of the present invention the compounds according to Formula 1 and Formula 2 may be used either simultaneously or sequentially in combination with a second compound, including those listed below.

Non-steroidal anti-inflammatory drugs, such as but not limited to: aspirin, choline salicylate, celecoxib, acetaminophen, diclofenac, flurbiprofen, ibuprofen, indomethacin, ketoprofen, meclofenamate, mefenamic acid, nabumetone, naproxen, piroxicam, rofecoxib, salicylates, sulindac, tolmetin, and valdecoxib.

Immunomodulatory agents, such as but not limited to: methotrexate, azathioprine, mitoxantrone, cladribin, cyclophosphamide, tacrorimus, methotrexate, cyclosporine, and hydroxychloroquine.

Antimalarials, such as but not limited to: chloroquine, quinine, amodiaquine, pyrimethamine, proguanil, mefloquine, atovaquone, primaquine, artemisinin, and halofantrine.

Antibiotics, such as but not limited to: minocycline, doxycycline, sulfonamides, and clindamycin.

Anti-TNF alpha agents, such as but not limited to: infliximab, adalimumab, certolizumab pegol, golimumab, thalidomide, lenalidomide, pomalidomide, and etanercept.

Anti-CD20 agents, such as but not limited to: rituximab, obinutuzumab, Ibritumomab tiuxetan, and tositumomab.

Antidiarrheals, such as but not limited to: lidamidine, diphenoxylate, loperamide, and quercetin.

Antidepressants, such as but not limited to: amitriptyline, clomipramine, doxepin nortriptyline and trimipramine.

Antipsychotics, such as but not limited to: droperidol, pimozide, chlorpromazine, thiothixene, loxapine, molindone, quetiapine, risperidone, sertindole and zotepine.

Antifungals, such as but not limited to: clotimazole, flucisoconazole, abafungin, micafugin, terbinafine, ciclopirox and tolnaftate.

Antihelminthics, such as but not limited to: mebendazole, levamisole, abamectin and suramine T lymphocyte activation inhibitors, such as but not limited to: voclosporin, peroxynitrite, and dasatinib.

Anti-IL-1 agents, such as but not limited to: anakinra and IL-1Ra.

Glucocorticoids, such as but not limited to: methyl prednisolone, prednisolone, dexamethasone, betamethasone, fluticasone propionate, budesonide, flunisolide, mometasone furoate, triamcinolone acetonide, rofleponide, ciclesonide, and butixocort propionate.

Anti-cytokine/chemokine monoclonal antibodies, such as but not limited to: basiliximab, daclizumab and secukinumab.

Sex steroids and receptor modulators, such as but not limited to: progesterone, progestins, androgen, estrogen, mifepristone and misoprostil.

Anti-cellular surface receptor monoclonal antibodies directed against cell surface receptors such as but not limited: CCR2, CCR5, IL7Ra and TSLPR.

Aminosalicylic acid derivatives such as but not limited to: sulfasalazine and mesalazine.

Anticholinergic agents, such as but not limited to: ipratropium, oxitropium, tiotropium, dextromethorphan, revatropate, pirenzepine, darifenacin, oxybutynin, mecamylamine, terodiline, tolterodine, otilonium, trospium chloride, and solifenacin.

Adrenergic agonists, such as but not limited to: salmeterol, salbutamol, clonidine, oxymetazoline, and dolbutamine.

Cholineric agonists, such as but not limited to: carbachol, epibatidine, galantamine, nicotine and varenicline, Corticosteroids, such as but not limited to: cortisone and hydrocortisone.

Antineoplastic chemotherapeutic agents, such as but not limited to: cisplatin cyclophosphamide, bleomycin, doxorubicin, etoposide, folinic acid, and vincristine.

Phosphodiesterase inhibitors, such as but not limited to: mesembrenone, rolipram, Ibudilast, piclamilast, luteolin, drotaverine, roflumilast, cilomilast, apremilast, and crisaborole.

Leukotriene pathway modulators, such as but not limited to: 3-[3-butylsulfanyl-1-[(4-chlorophenyl)methyl]-5-propan-2-yl-indol-2-yl]-2,2-dimethyl-propanoic acid, baicalein, caffeic acid, curcumin, hyperforin, and zileuton.

Monoclonal antibodies directed against human immunoglobulins, such as but not limited to: omalizumab.

Adrenergic antagonists, such as but not limited to: alfluosin, idazoxan, labetalol, phentolamine, trazadone, propranolol and atenolol.

Calcium channel antagonists, such as but not limited to: amelodipine, nifedapine, verapamil, diltiazem, and mibefradil.

Dopamine agonists, such as but not limited to: aripiprazole, bromocriptine, bupropion, cabergoline, lisuride, and roxindole.

Serotonin agonists, such as but not limited to: cabergoline, cisapride, gepirone, lorcaserin, and naratriptan.

Dopamine antagonists, such as but not limited to: amoxipine, bromopride, butaclamol, eticlopride, olanzapine, tiapride, and ziprasidone.

Serotonin antagonists, such as but not limited to: cyproheptadine, ketanserin, metergoline, methdilazine, oxetorone, and tropisetron.

Monoamine reuptake inhibitors, such as but limited to: aminaptine, citalopram, edivoxetine, hyperforin, mazindol, and viloxazine.

Protease inhibitors, such as but not limited to: amastatin, bestatin, and gabexate.

Histamine receptor antagonists, such as but not limited to: acrivastine, brompheniramine, cetirizine, cimetidine, ciproxifan, clobenprobit, cyclizine, carebastine, cyproheptadine, ebastine, epinastine, efletirizine, fexofenadine, and thioperamide.

Proton pump inhibitors, such as but not limited to; omeprazole, lansoprazole, pantoprazole and rabeprazole.

HMG-CoA reductase inhibitors, such as but not limited to: atorvastatin, fluastatin, lovastatin, and simvastatin.

Administration of the therapeutic agent may be by any suitable means. In some embodiments, the one or more therapeutic agents are administered by oral administration. In some embodiments, the one or more therapeutic agents are administered by transdermal administration. In some embodiments, the one or more therapeutic agents are administered by injection or intravenous infusion. In one embodiment, the one or more therapeutic agents are administered topically to a mucosal, dermal or ocular tissue.

If combinations of agents are administered as separate compositions, they may be administered by the same route or by different routes. If combinations of agents are administered in a single composition, they may be administered by any suitable route. In some embodiments, combinations of agents are administered as a single composition by oral administration. In some embodiments, combinations of agents are administered as a single composition by transdermal administration. In some embodiments, the combinations of agent are administered as a single composition by injection. In some embodiments, the combinations of agent are administered as a single composition topically.

In one embodiment of the present invention the compounds of Formula 1 and Formula 2 may contain asymmetric or chiral centers, and, therefore, exist in different stereoisomeric forms. For example, N-[2-(diethylamino)ethyl]-N-ethyl-3-(4-methoxyphenoxy)propanamide a compound according Formula 1 that possesses a chiral center at the second nitrogen atom and thus has two stereoisomer forms. It is intended that all stereoisomeric forms of the compounds of Formula I and Formula 2 form part of the present invention, including but not limited to: diastereomers, enantiomers, and atropisomers as well as mixtures thereof such as racemic mixtures. In addition, the present invention embraces all geometric and positional isomers. For example, if a compound of Formula I or Formula 2 incorporates a double bond or a fused ring, both the cis- and trans-forms, as well as mixtures, are embraced within the scope of the invention. Both the single positional isomers and mixture of positional isomers are also within the scope of the present invention.

In one embodiment of the present invention, compounds of Formula 1 and Formula 2 may exist in different tautomeric forms, and all such forms are embraced within the scope of the invention, as defined by the claims.

In one embodiment of the present invention the therapeutically effective dose is from about 0.01 mg to about 5,000 mg per day of a compound provided herein. The pharmaceutical compositions therefore should provide a dosage of from about 0.01 mg to about 5000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient. In another embodiment of the present invention the pharmaceutical dosage unit forms are prepared to provide a topical solution from about 0.01% to 10% of the compounds.

IV. EXAMPLES

To determine the ability of compounds according to Formula 1 and Formula 2 to inhibit CCL2 signal transduction through CCL2/CCR2 axis signaling pathway using a functional assay, cultivated human monocytes, PBMCs or endothelial cells were treated with purified human recombinant CCL2 protein (30 ng/mL) and the expression of various cytokines, cell adhesion and angiogenesis promoting proteins and pathway intermediate genes, known to be upregulated by CCL2, were determined by well-known methods as described below.

Freshly isolated Human PBMCs or CD14+ monocytes from healthy volunteers were isolated and cultured at $1\times10^6$ cells/ml in RPMI-1640 medium (GIBCO® Inc. Carlsbad, Calif., USA) supplemented with 20% fetal bovine serum and 1% streptomycin/penicillin. Human Aortic Endothelial Cells (catalog number: C0065C), Medium 200PRF and LSGS supplement were obtained from (ThermoFischer Scientific; San Diego, Calif., USA) and cultivated according to suppliers protocol. The endothelial cell suspensions were plated in 6-well culture plates and cultured at $1\times10^5$ cells/ml in Medium 200PRF supplemented with LSGS and incubated in a 37° C., 5% $CO_2$/95% air, humidified cell culture incubator for 72 hours at 37° C. in 5% $CO_2$ humidified incubator prior to stimulation. The cultures of PBMC, CD+14 monocytes and endothelial cells were stimulated with 30 ng/ml of CCL2 (R&D SYSTEMS®, Minneapolis, Minn. USA) for 6-18 hrs. Cell suspensions without CCL2 stimulation were used as a baseline control for the experiments. Cell cultures were treated with various exemplar compounds according to Formula 1 and Formula 2 at several concentrations. As a known positive control for CCL2/CCR2 pathways inhibitory moderation, a blocking antibody to human CCL2 (R&D SYSTEMS®, Minneapolis, Minn. USA) was used (10 ug/ml) that prevents binding of CCL2 to CCR2 receptor and therefore blocks signal transduction through the CCL2/CCR2 signaling pathways.

The expression of specific genes known to be up-regulated by CCL2 through the CCL2/CCR2 signaling pathways were measured by quantitative RNAseq method according to standard protocols (97,98) using the Illumina Hi Seq 2000 (Illumina Inc; San Diego, Calif.) using bar-coded multiplexing and a 75 bp read length with median sequencing reads per replicate sample of 20 million. Cell cultures were incubated for 6-18 hrs with compounds of the invention or with media alone (control cell cultures) prior to extraction of RNA using TRIZOL® reagent (ThermoFisher Scientific; San Diego, Calif.). Total RNA isolated was isolated according to the manufacturer's protocol (Invitrogen; Carlsbad, Calif.). RNA quality and quantity were assessed with the RNA 6000 Nano Kit (Agilent; Santa Clara, Calif.). The cDNA libraries for sequencing were prepared from Poly A selected total RNA. Data were expressed as fragments per kilobase of exon per million fragments mapped (FPKM). FPKM filtering cutoff of 0.5 in at least two of each of the triplicate samples was used to determine expressed transcripts in control cells vs cells treated with test compounds. Upregulated genes were defined as those with increased expression more than 2 fold after treatment of cells with CCL2. Differential transcript expression was then computed using Cuffdiff2 (99). In addition., all sample quantitation assays were standardized to the expression level of known human "housekeeping genes" using Log2 transformed FPKM values, which are graphically expressed as Relative Expression based on percent of control. The "housekeeping genes," [e.g. ribosomal protein large P1 (RPLP1) and glyceraldehyde-3-phosphate dehydrogenase (GAPDH), etc.] are constitutively expressed and not upregulated by CCL2. All studies were performed in triplicate. Examples of the results of these experiments are shown in FIGS. 2 and 3. These experiments demonstrate that the increased expression of specific downstream genes associated with CCL2/CCR2 dependent signaling induced by CCL2 in cultivated cells are inhibited by the compounds of the instant invention.

The concentration of key proteins known to be associated with inflammation, cell adhesion and vascular proliferation that are increased by CCL2 in monocytes, fibroblasts, endothelial cells and PBMCs through the via CCL2/CCR2 axis signal transduction were measured in control cells vs those treated with the test compounds, using commercially obtained enzyme-linked immunosorbent assay (ELISA) kits (R&D SYSTEMS®, Minneapolis, Minn. USA) according to the manufacturer's instructions. The levels of the proteins in the cell culture supernatant or cell pellet lysates stimulated with CCL2 alone or treated with CCL2 along with various compounds was measured, as well as with the positive controls. Experiments were performed in triplicate. Examples of the results of these experiments are shown in FIGS. 1, 4 and 5.

The results of the experiments herein demonstrate that compounds according to Formula 1 and Formula 2 inhibit the biological effects of CCL2, for example by decreasing the production of CCL2 induced pro-inflammatory cytokines, cellular adhesion promoting molecules and proteins inducing vascular proliferation, as well as decreasing the expression of other intermediate genes associated with the CCL2/CCR2 signaling cascades in human cells. Therefore, the compounds according to Formula I and Formula 2 are useful in treatment of various disorders associated with CCL2/CCR2 axis signaling.

REFERENCES

1. Charo I F, Ransohoff R M. NEJM 2006 Feb. 9; 354(6): 610-21
2. Yadav A, Saini V, Arora S Clinica chimica acta; 2010 Nov. 11; 411(21-22):1570-9

3. Ashida N, Arai H, Yamasaki M, Kita T. J Biol Chem 2001 May 11; 276(19):16555-60
4. Gerszten R E, Friedrich E B, Matsui T, et al. J Biol Chem 2001 Jul. 20; 276(29):26846-51
5. Ferreira A M, Isaacs H, Hayflick J S, et al. Microcirculation 2006 September; 13(6):439-56
6. Weber C, Alon R, Moser B, Springer T A. J Cell Biol 1996 August; 134(4):1063-73
7. Hong K H, Ryu J, Han K H Blood 2005 Feb. 15; 105(4):1405-7
8. Dimberg A. Current topics in microbiology and immunology 2010; 341:59-80
9. Viedt C, Dechend R, Fei J, et al. JASN 2002 June; 13(6):1534-47
10. Biswas S K, Sodhi A. J Interferon & cytokine research 2002 May; 22(5):527-38
11. Viedt C, Vogel J, Athanasiou T, et al. Arterio Thromb Vasc Biol 2002 Jun. 1; 22(6):914-20
12. Zhang X, Liu X, Shang H, et al. Acta biochimica et biophysica Sinica 2011 October; 43(10):787-95
13. Dawson J, Miltz W, Mir A K, Expert opinion on therapeutic targets 2003 February; 7(1):35-48
14. Deshmane S L, Kremlev S, Amini S, et al. J Interferon & Cytokine Research 2009 June; 29(6):313-26
15. Monteclaro F S, Charo I F. J Biol Chem 1997 Sep. 12; 272(37):23186-90
16. Gu L, Tseng S C, Rollins B J. Chemical immunology 1999; 72:7-29
17. Maus U, Henning S, Wenschuh H, et al. American J Physiol. 2002 December; 283(6):H2584-91
18. Yang E J, Choi E, Ko J, et al. J Cell Physiology 2012 June; 227(6):2567-77
19. Nibbs R J, Wylie S M, Pragnell I B, aet al. J Biol Chem 1997 May 9; 272(19):12495-504
20. Kashiwazaki M, Tanaka T, Kanda H, et al. International immunology 2003 October; 15(10):1219-27
21. Fra A M, Locati M, Otero K, at al. J Immunol 2003 Mar. 1; 170(5):2279-82
22. Comerford I, Litchfield W, Harata-Lee Y, et al. BioEssays 2007 March; 29(3):237-47
23. Sozzani S, Locati M, Zhou D, et al. J Leukocyte boil 1995 May; 57(5):788-94
24. Jimenez-Sainz M C, Fast B, Mayor F Jr, at al. Mol Pharmacology 2003 September; 64(3):773-82
25. Denis C, Sauliere A, Galandrin S, Senard J M, Gales C. Current Pharm Design 2012; 18(2):128-44
26. Turner S J, Domin J, Waterfield M D, et al. J Biol Chem 1998 Oct. 2; 273(40):25987-95
27. Curnock A P, Logan M K, Ward S G Immunology 2002 February; 105(2):125-36
28. Wymann M P, Pirola L Biochimica et biophysica acta 1998 Dec. 8; 1436(1-2):127-50
29. Hawkins P T, Anderson K E, Davidson K, Set al. Biochem Society Trans 2006 November; 34(Pt 5):647-62
30. Welch H C, Coadwell W J, Stephens L R, et al. FEBS letters 2003 Jul. 3; 546(1):93-7
31. Cain R J, Ridley A J Biology of the Cell 2009 January; 101(1):13-29
32. Weber K S, Klickstein L B, Weber P C, Euro J Immunol 1998 July; 28(7):2245-51
33. Sotsios Y, Ward S G Immunological reviews 2000 October; 177:217-35
34. Kolluri R, Tolias K F, Carpenter C L, et al. PNAS (USA) 1996 May 28; 93(11):5615-8
35. Mukai Y, Iwaya K, Ogawa H, Mukai K Biochem Biophys Res Comm 2005 Aug. 26; 334(2):395-402
36. Carr M W, Alon R, Springer T A. Immunity 1996 February; 4(2):179-87
37. Weber K S, Klickstein L B, Weber C. Mol Biol Cell 1999 April; 10(4):861-73
38. Pepper M S. Arteriosclerosis, thrombosis, and vascular biology 2001 July; 21(7):1104-17
39. Bauvois B. Oncogene 2004 Jan. 15; 23(2):317-29
40. Galvez B G, Genis L, Matias-Roman S, et al. J Biol Chem 2005 Jan. 14; 280(2):1292-8
41. Stamatovic S M, Keep R F, Kunkel S L, Andjelkovic A V. J Cell Sci 2003 Nov. 15; 116(Pt 22):4615-28
42. Song L, Pachter J S. Microvascular Res 2004 January; 67(1):78-89
43. Stamatovic S M, Shakui P, Keep R F, et al. J Cerebral blood flow and metabolism 2005 May; 25(5):593-606
44. Lai C H, Kuo K H, Leo J M. Brain research reviews 2005 Dec. 1; 50(1):7-13
45. Stamatovic S M, Dimitrijevic O B, Keep R F, et al. J Biol Chem 2006 Mar. 31; 281(13):8379-88
46. Song L, Ge S, Pachter J S. Blood 2007 Feb. 15; 109(4):1515-23
47. Stamatovic S M, Keep R F, Wang M M, et al. J Biol Chem 2009 Jul. 10; 284(28):19053-66
48. Schneeberger E E, Lynch R D. Am J Physiology 2004 June; 286(6):C1213-28
49. Cambien B, Pomeranz M, Millet M A, et al. Blood 2001 Jan. 15; 97(2):359-66
50. Wain J H, Kirby J A, Ali S. Clin Exp Immunology 2002 March; 127(3):436-44
51. Oda N, Abe M, Sato Y. J Cell Physiology 1999 February; 178(2):121-32
52. Stamatovic S M, Keep R F, Mostarica-Stojkovic M, et al. J Immunology 2006 Aug. 15; 177(4):2651-61
53. Mehrad B, Keane M P, Strieter R M. Thrombo Haemost 2007 May; 97(5):755-62
54. Werle M, Schmal U, Hanna K, Kreuzer J. Cardiovascular Res 2002 November; 56(2):284-92
55. Pulverer B J, Kyriakis J M, Avruch J. et al Nature 1991 Oct. 17; 353(6345):670-4
56. Yoon S, Seger R. Growth Factors 2006 March; 24(1): 21-44
57. Biswas S K, Sodhi A, Paul S. Nitric Oxide 2001 December; 5(6):566-79
58. Kleinert H, Pautz A, Linker K et al. Euro J Pharmacol 2004 Oct. 1; 500(1-3):255-66
59. Tesch G H. Am J Physiology. Renal physiology 2008 April; 294(4):F697-701
60. Viedt C, Orth S R. Nephrology, dialysis, transplantation 2002 December; 17(12):2043-7
61. Giunti S, Pinach S, Arnaldi L, et al. Kidney Internat 2006 March; 69(5):856-63
62. Jiang Y, Beller D I, Frendl G. J Immunology 1992 Apr. 15; 148(8):2423-8
63. Yamamoto T, Eckes B, Mauch C, et al. J Immunology 2000 Jun. 15; 164(12):6174-9
64. Gavrilin M A, Deucher M F, Boeckman F. et al. Biochem Biophys Res Com 2000 Oct. 14; 277(1):37-42
65. Biswas S K, Sodhi A. Internat Immunopharm 2002 July; 2(8):1095-107
66. Pahl H L. Oncogene 1999 Nov. 22; 18(49):6853-66
67. Liu H, Sidiropoulos P, Song G, at al. J Immunology 2000 Apr. 15; 164(8):4277-85
68. Niu J, Azfer A, Zhelyabovska O, et al. J Biol Chem 2008 May 23; 283(21):14542-51
69. Ke Q, Costa M. Mol Pharmacology 2006 November; 70(5):1469-80

70. Richard D E, Berra E, Gothie E. et al. J Biol Chem 1999 Nov. 12; 274(46):32631-7
71. Younce C W, Kolattukudy P E. Biochem Journal 2010 Jan. 27; 426(1):43-53
72. Roy A, Kolattukudy P E. Cellular Signalling 2012 November; 24(11):2123-31
73. Younce C W, Wang K, Kolattukudy P E. Cardiovascular Res 2010 Sep. 1; 87(4):665-74
74. Rollins B J, Walz A, Baggiolini M. Blood 1991 Aug. 15; 78(4):1112-6
75. Zhou L, Azfer A, Niu J. et al. Circulation Res 2006 May 12; 98(9):1177-85
76. Bidzhekov K, Zernecke A, Weber C. Circulation Res 2006 May 12; 98(9):1107-9
77. Fenoglio C1, Galimberti D, Lovati C, et al. Neurobiol Aging. 2004 October; 25(9):1169-73.
78. Rózyk K J1, Plusa T, Kuna P, Pirozyńska E. Immunol Lett. 1997 June; 58(1):47-52.
79. Cho M L1, Kim J Y, Ko H J, Kim Y H, et al. Autoimmunity. 2004 February; 37(1):77-80.
80. Miotto D, Christodoulopoulos P, et al. J Allergy Clin Immunol. 2001 April; 107(4):664-70.
81. Fujimoto H1, Sangai T, Ishii G, et al. Int J Cancer. 2009 Sep. 15; 125(6):1276-84.
82. Tabara Y1, Kohara K, Yamamoto Y, et al. Hypertens Res. 2003 September; 26(9):677-83.
83. Vestergaard C, Just H, Baumgartner J, et al. ACTA Derm Venereol. 2004; 84:353-358.
84. Mori H1, Kaneko Y, Narita I, et al. Clin Exp Nephrol. 2005 December; 9(4):297-303.
85. Park B L, Kim Y J, Cheong H S, et al. Exp Mol Med. 2006 Dec. 31; 38(6):694-702.
86. Sorensen T L, Ransohoff R M, Strieter R M, Sellebjerg F. Eur J Neurol. 2004 July; 11(7):445-9.
87. Papachristou G I, Sass D A, Avula H, et al. Clin Gastroenterol Hepatol. 2005 May; 3(5):475-81.
88. Mehta N N, Li K, Szapary P, Krueger J, Brodmerkel C. J Transl Med. 2013 Aug. 22; 11:194.
89. Hartl D, Griese M, Nicolai T, et al. Respir Res. 2005 Aug. 11; 6:93.
90. Zhang L, Yu M, Deng J, et al. Yonsei Med J. 2015 July; 56(4):1134-42.
91. Karrer S, Bosserhoff A K, Weiderer P, et al. J Invest Dermatol. 2005 January; 124(1):92-8.
92. Iwamoto N, Kawakami A, Arima K, et al. Rheumatology (Oxford). 2010 August; 49(8):1472-8.
93. Noris M, Bernasconi S, Casiraghi F, et al. Lab Invest. 1995 December; 73(6):804-9.
94. Ahad M A1, Missotten T, Abdallah A, et al. Mol Vis. 2007 Mar. 23; 13:388-96.
95. Letendre S1, Marquie-Beck J, Singh K K, et al. J Neuroimmunol. 2004 December; 157(1-2):193-6.
96. Elena Sierra-Filardi, Concha Nieto, Angeles Dominguez-Soto, et al. J Immunol. Apr. 15, 2014, 192 (8) 3858-3867.
97. Nagalakshmi U, Waern K, Synder M. Curr Protoc Mol Biol. 2010 January; 4.11.1-4.11.13.
98. Wang C, Gong B, Buschel P R, et al. Nat Biotechol. 2014 August; 32: 926-932.
99. Trapnell C, Hendrickson D G, Sauvageau M, et al. Nat Biotechol. 2013 January; 34(1): 46-53.

What is claimed is:

1. A method of inhibiting the biological activity of CCL2 in a mammal comprising administering to a mammal an effective amount of a compound according to Formula 2 below:

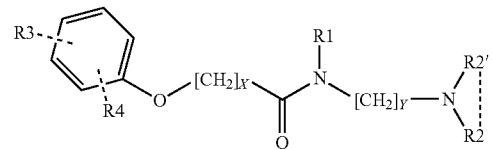

wherein
Y is 1-3
R1 is methyl, ethyl, or $CF_3$;
R2 and R2' are independently selected from methyl, ethyl, n-propyl, 2-propyl, tert-butyl, alkoxy and hydrogen;
R3 is methyl, ethyl, hydroxyl, caboxylic acid, alkoxy, haloalkyl or hydrogen; and
R4 is hydrogen, hydroxyl or halogen,
or a pharmaceutically acceptable salt, addition compound or pro-drug thereof.

2. The method of claim 1, wherein the compound inhibits the biological activity CCL2 caused by the interaction of CCL2 with CCR2.

3. The method of claim 1, wherein the compound reduces the expression of at least one protein component of the CCL2/CCR2 signal transduction process.

4. A method of treatment comprising administering to a mammal in need thereof, including a human, a therapeutically effective amount of the compound of Formula 2 below:

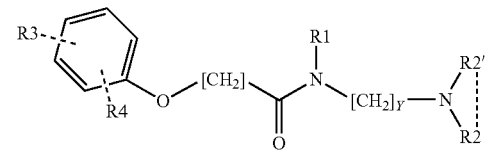

wherein
Y is 1-3
R1 is methyl, ethyl, or $CF_3$;
R2 and R2' are independently selected from methyl, ethyl, n-propyl, 2-propyl, tert-butyl, alkoxy and hydrogen;
R3 is methyl, ethyl, hydroxyl, carboxylic acid, alkoxy, haloalkyl or hydrogen; and
R4 is hydrogen, hydroxyl, or halogen,
or a pharmaceutically acceptable salt, addition compound or pro-drug thereof,
for treatment of a disease or condition associated with increased CCL2 biological activity selected from the group consisting of Rheumatoid Arthritis, Dermatitis, Inflammation, and Psoriasis.

5. The method of claim 4, further comprising administering at least one other compound selected from the group consisting of Non-steroidal anti-inflammatory drugs, Immunomodulatory agents, Anti-malarials, Antibiotics, Anti-TNF alpha agents, Anti-CD20 agents, Anti-diarrheal drugs, Antidepressants, Anti-psychotics, Anti-fungals, Anti-helminthics, T lymphocyte activation inhibitors, Anti-IL-1 agents, Glucocorticoids, Anti-cytokine/chemokine monoclonal antibodies, Sex steroids and receptor modulators, Anti-cellular surface receptor monoclonal antibodies, Aminosalicylic acid derivatives, Anticholinergic agents, Adrenergic agonists, Corticosteroids, Anti-neoplastic chemotherapeutic agents, Phosphodiesterase inhibitors, Leukotriene pathway modulators, Monoclonal antibodies directed against human immunoglobulins, Adrenergic antagonists, Calcium channel antagonists, Dopamine agonists, Serotonin agonists, Dopamine antagonists, Serotonin antagonists, Monoamine reuptake inhibitors, Protease inhibitors, Histamine antagonists, Proton pump inhibitors, and HMG-CoA reductase inhibitors.

6. A method of inhibiting the biological activity of CCL2 in a mammal comprising administering to a mammal in need thereof, including a human, an effective amount of a compound according to Formula 3 below:

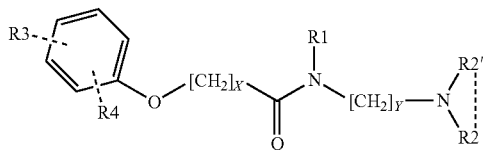

wherein
X is 1-3;
Y is 1-3;
R1 is methyl, ethyl, propyl, butyl, haloalkyl, or hydrogen;
R2 and R2' are independently selected from methyl, ethyl, propyl, butyl, alkoxy, haloalkyl, and hydrogen or R2 and R2' may be fused into a heterocyclic ring with 5 or 6 members;
R3 is methyl, ethyl, hydroxyl, alkoxy, carboxylic acid, haloalkyl or hydrogen; and
R4 is hydrogen, hydroxyl or halogen,
or a pharmaceutically acceptable salt, addition compound or pro-drug thereof.

7. The method of claim 6, wherein the compound inhibits the biological activity CCL2 caused by the interaction of CCL2 with CCR2.

8. The method of claim 6, wherein the compound reduces the expression of at least one protein component of the CCL2/CCR2 signal transduction process.

9. The method of claim 6, wherein the amount of Formula 3 is a therapeutically effective amount and wherein the inhibition of biological activity of CCL2 is for treatment of a disease or condition associated with increased biological activity of CCL2 selected from the group consisting of Rheumatoid Arthritis, Dermatitis, Inflammation, and Psoriasis.

10. The method of claim 9, further comprising administering at least one other compound selected from the group consisting of Non-steroidal anti-inflammatory drugs, Immunomodulatory agents, Anti-malarials, Antibiotics, Anti-TNF alpha agents, Anti-CD20 agents, Anti-diarrheal drugs, Anti-depressants, Anti-psychotics, Anti-fungals, Anti-helminthics, T lymphocyte activation inhibitors, Anti-IL-1 agents, Glucocorticoids, Anti-cytokine/chemokine monoclonal antibodies, Sex steroids and receptor modulators, Anti-cellular surface receptor monoclonal antibodies, Aminosalicylic acid derivatives, Anticholinergic agents, Adrenergic agonists, Corticosteroids, Anti-neoplastic chemotherapeutic agents, Phosphodiesterase inhibitors, Leukotriene pathway modulators, Monoclonal antibodies directed against human immunoglobulins, Adrenergic antagonists, Calcium channel antagonists, Dopamine agonists, Serotonin agonists, Dopamine antagonists, Serotonin antagonists, Monoamine reuptake inhibitors, Protease inhibitors, Histamine antagonists, Proton pump inhibitors, and HMG-CoA reductase inhibitors.

11. The method according to claim 6, wherein the inhibition of the biological activity of CCL2 decreases angiogenesis and/or leukocyte adhesion and/or leukocyte transendothelial migration.

12. The method according to claim 6, wherein the inhibition of the biological activity of CCL2 inhibits the production of VCAM-1 and/or ICAM-1 and/or VEGF-A and/or MMP-2.

13. The method according to claim 6, wherein the inhibition of the biological activity of CCL2 decreases inflammation induced by CCL2.

14. The method according to claim 6, wherein the inhibition of the biological activity of CCL2 decreases the production of Interleukin 1 and/or Interleukin 6 and/or TNF alpha and/or Interferon gamma.

15. The method of claim 6, wherein the compound is a racemic mixture or a specific stereoisomer.

* * * * *